US012134071B2

(12) United States Patent
Hoyda et al.

(10) Patent No.: US 12,134,071 B2
(45) Date of Patent: Nov. 5, 2024

(54) AIR PURIFYING MACHINE AND PROCESS

(71) Applicant: AWE SOLUTIONS INC., Great Neck, NY (US)

(72) Inventors: Serge B. Hoyda, Great Neck, NY (US); Corey Lee MacPhee, New Brunswick (CA); Gregg Russell Dickinson, Briarwood, NY (US)

(73) Assignee: AWE SOLUTIONS INC., Great Neck, NY (US)

( * ) Notice: Subject to any disclaimer, the term of this patent is extended or adjusted under 35 U.S.C. 154(b) by 1105 days.

(21) Appl. No.: 16/792,159

(22) Filed: Feb. 14, 2020

(65) Prior Publication Data

US 2020/0179873 A1 Jun. 11, 2020

Related U.S. Application Data

(63) Continuation-in-part of application No. 16/231,396, filed on Dec. 22, 2018, now Pat. No. 10,969,125.
(Continued)

(51) Int. Cl.
*A61L 9/14* (2006.01)
*B01D 53/34* (2006.01)
*B01D 53/84* (2006.01)

(52) U.S. Cl.
CPC .............. *B01D 53/84* (2013.01); *A61L 9/145* (2013.01); *B01D 53/346* (2013.01);
(Continued)

(58) Field of Classification Search
CPC ............... A61L 9/145; A61L 9/04; A61L 9/14
See application file for complete search history.

(56) References Cited

U.S. PATENT DOCUMENTS 1,102,377 A 7/1914 Wilton
2,638,644 A 5/1953 Rauhut
(Continued)

FOREIGN PATENT DOCUMENTS

DE 101 00 674 A1 8/2002
DE 10 2016 120 534 B3 11/2017
(Continued)

OTHER PUBLICATIONS

First Examination Report in Indian Office Action No. 202027030194 dated Apr. 7, 2022 with English translation.
(Continued)

*Primary Examiner* — Donald R Spamer
(74) *Attorney, Agent, or Firm* — Collard & Roe, P.C.; William Collard

(57) ABSTRACT

At least one embodiment relates to an air purifying machine comprising at least one housing and a plurality of cores wherein each core is disposed in the housing. There is also at least one fan disposed in the housing. In addition, there is at least one pump disposed in the housing, wherein the pump is configured to circulate a fluid inside of the housing. The cores comprise at least two cores disposed inside of the housing comprising a first core and a second core, wherein the second core is disposed inside of said first core and wherein the second core is not concentric with the first core. The non-concentric nature of the cores creates a compression location at a point where the two cores are disposed closest to each other. This compression location creates a higher-pressure location for air flow around the cores. The different size of the openings for air to circulate between the cores creates air turbulence which results in greater interaction between the incoming air and the bioreactive fluid solution inside of the air purification system.

15 Claims, 21 Drawing Sheets

US 12,134,071 B2
Page 2

Related U.S. Application Data

(60) Provisional application No. 62/711,297, filed on Jul. 27, 2018, provisional application No. 62/610,092, filed on Dec. 22, 2017.

(52) U.S. Cl.
CPC ...... *A61L 2209/111* (2013.01); *A61L 2209/21* (2013.01); *A61L 2209/22* (2013.01)

(56) References Cited

U.S. PATENT DOCUMENTS

| | | | |
|---|---|---|---|
| 4,689,302 A | 8/1987 | Goldberg et al. | |
| 4,746,336 A | 5/1988 | Mignot | |
| 5,589,132 A | 12/1996 | Zippel | |
| 5,656,242 A | 8/1997 | Morrow et al. | |
| 5,756,899 A | 5/1998 | Ugai et al. | |
| 6,053,968 A | 4/2000 | Miller | |
| 6,500,244 B2 | 12/2002 | Sanchez | |
| 6,589,489 B2 | 7/2003 | Morrow et al. | |
| 6,810,732 B2 | 11/2004 | Shon | |
| 6,916,630 B2 | 7/2005 | Sofer | |
| 7,112,232 B2 | 9/2006 | Chang et al. | |
| 7,147,692 B2 | 12/2006 | Fornai et al. | |
| 7,665,358 B2 | 2/2010 | Calabrese | |
| 7,722,708 B2 | 5/2010 | Powell, Jr. et al. | |
| 8,083,837 B2 | 12/2011 | Mazzanti et al. | |
| 8,357,359 B2 | 1/2013 | Woo et al. | |
| 8,444,922 B2 | 5/2013 | Kusuura | |
| 8,748,167 B2 | 6/2014 | Greene et al. | |
| 9,044,700 B2 | 6/2015 | Gruenbacher et al. | |
| 9,327,223 B2 | 5/2016 | Gruenbacher et al. | |
| 9,573,088 B2 | 2/2017 | Gruenbacher et al. | |
| 9,579,597 B2 | 2/2017 | Gruenbacher et al. | |
| 10,969,125 B2 * | 4/2021 | Hoyda | F24F 8/133 |
| 2004/0184949 A1 | 9/2004 | McEllen | |
| 2006/0097411 A1 | 5/2006 | Kim | |
| 2006/0169141 A1 | 8/2006 | Yuen | |
| 2007/0122320 A1 | 5/2007 | Pletcher et al. | |
| 2008/0156015 A1 | 7/2008 | Meyerholtz et al. | |
| 2008/0271527 A1 | 11/2008 | Hewitt | |
| 2010/0047117 A1 | 2/2010 | Bernard | |
| 2010/0154534 A1 | 6/2010 | Hampton | |
| 2011/0150814 A1 | 6/2011 | Woo et al. | |
| 2011/0303093 A1 | 12/2011 | Jeung | |
| 2011/0318817 A1 * | 12/2011 | Greene | A61L 9/044 435/262.5 |
| 2012/0167660 A1 | 7/2012 | Calcote | |
| 2012/0183488 A1 | 7/2012 | Woo et al. | |
| 2012/0183489 A1 | 7/2012 | Woo et al. | |
| 2013/0085204 A1 | 4/2013 | Hollingshead et al. | |
| 2014/0208781 A1 | 7/2014 | Broadbent | |
| 2015/0004064 A1 | 1/2015 | Lee | |
| 2015/0266031 A1 | 9/2015 | Mills et al. | |
| 2016/0061646 A1 | 3/2016 | Mestivier et al. | |
| 2017/0122600 A1 | 5/2017 | Son et al. | |
| 2019/0203960 A1 | 7/2019 | Hoyda et al. | |
| 2020/0064175 A1 | 2/2020 | Krammer et al. | |
| 2020/0179873 A1 | 6/2020 | Hoyda et al. | |
| 2022/0397440 A1 | 12/2022 | Broadbent | |

FOREIGN PATENT DOCUMENTS

| | | | |
|---|---|---|---|
| EP | 0 328 782 A1 | 8/1989 | |
| KR | 1997-0030147 A | 6/1997 | |
| WO | 9407122 A1 | 3/1994 | |
| WO | 2004008034 A1 | 1/2004 | |
| WO | 2014162006 A1 | 10/2014 | |
| WO | 2021190749 A1 | 9/2021 | |

OTHER PUBLICATIONS

U.S. Office Action in U.S. Appl. No. 17/181,604 dated Aug. 31, 2023.
U.S. Office Action in U.S. Appl. No. 17/852,341 dated Sep. 12, 2023.
U.S. Office Action in U.S. Appl. No. 16/231,396 dated Oct. 30, 2019.
U.S. Final Office Action in U.S. Appl. No. 16/231,396 dated Apr. 20, 2020.
U.S. Advisory Action in U.S. Appl. No. 16/231,396 dated May 18, 2020.
U.S. Office Action in U.S. Appl. No. 16/231,396 dated Jun. 26, 2020.
U.S. Notice of Allowance in U.S. Appl. No. 16/231,396 dated Oct. 16,.
U.S. Notice of Allowance in U.S. Appl. No. 16/231,396 dated Nov. 23, 2020.
International Search Report of PCT/US2018/067402, issued Mar. 28, 2019.
Written Opinion of the International Searching Authority of PCT/US2018/067402, issued Mar. 28, 2019.
International Preliminary Report on Patentability with Written Opinion of the International Searching Authority of PCT/US2018/067402, mailed Jul. 2, 2020.
Extended European Search Report of European Application No. 18892900.4 dated Oct. 8, 2021.
International Search Report of PCT/US2021/18133 mailed Jun. 15, 2021.
Notice of Transmittal of the International Search Report of PCT/US2021/18133 mailed Jun. 15, 2021.
Written Opinion of the International Searching Authority of PCT/US2021/18133 mailed Jun. 15, 2021.
International Preliminary Report on Patentability with Written Opinion of the International Searching Authority of PCT/US2021/018133 dated Aug. 11, 2022.
Second Chinese Office Action in Chinese Patent Application 201880089590.6 dated Jun. 29, 2022.
International Search Report in PCT/US23/17771 dated Jun. 21, 2023.
Written Opinion of the Interntional Searching Authority in PCT/US23/17771 dated Jun. 21, 2023.
Notification of Transmittal of the International Search Report and the Written Opinion of the International Searching Authority in PCT/US23/17771 dated Jun. 21, 2023.
Notice of Allowance in Chinese Application No. 201880089590.6 dated Oct. 21, 2022.
Chinese Office Action in Chinese Application No. 201880089590.6 dated Oct. 27, 2021 with English translation.
International Search Report in PCT/US22/35385 dated Oct. 5, 2022.
Written Opinion in PCT/US22/35385 dated Oct. 5, 2022.
Canadian Examination Report in Canadian Patent Application Serial No. 3,167,873, dated Oct. 19, 2023.
Canadian Examination Report in Canadian Patent Application Serial No. 3,127,077, dated Nov. 1, 2023.
Canadian Examiner's Report in Canadian Application No. 3,127,077 dated Aug. 9, 2024.
U.S. Non-Final Office Action in U.S. Appl. No. 17/715,694 dated Sep. 11, 2024.

* cited by examiner

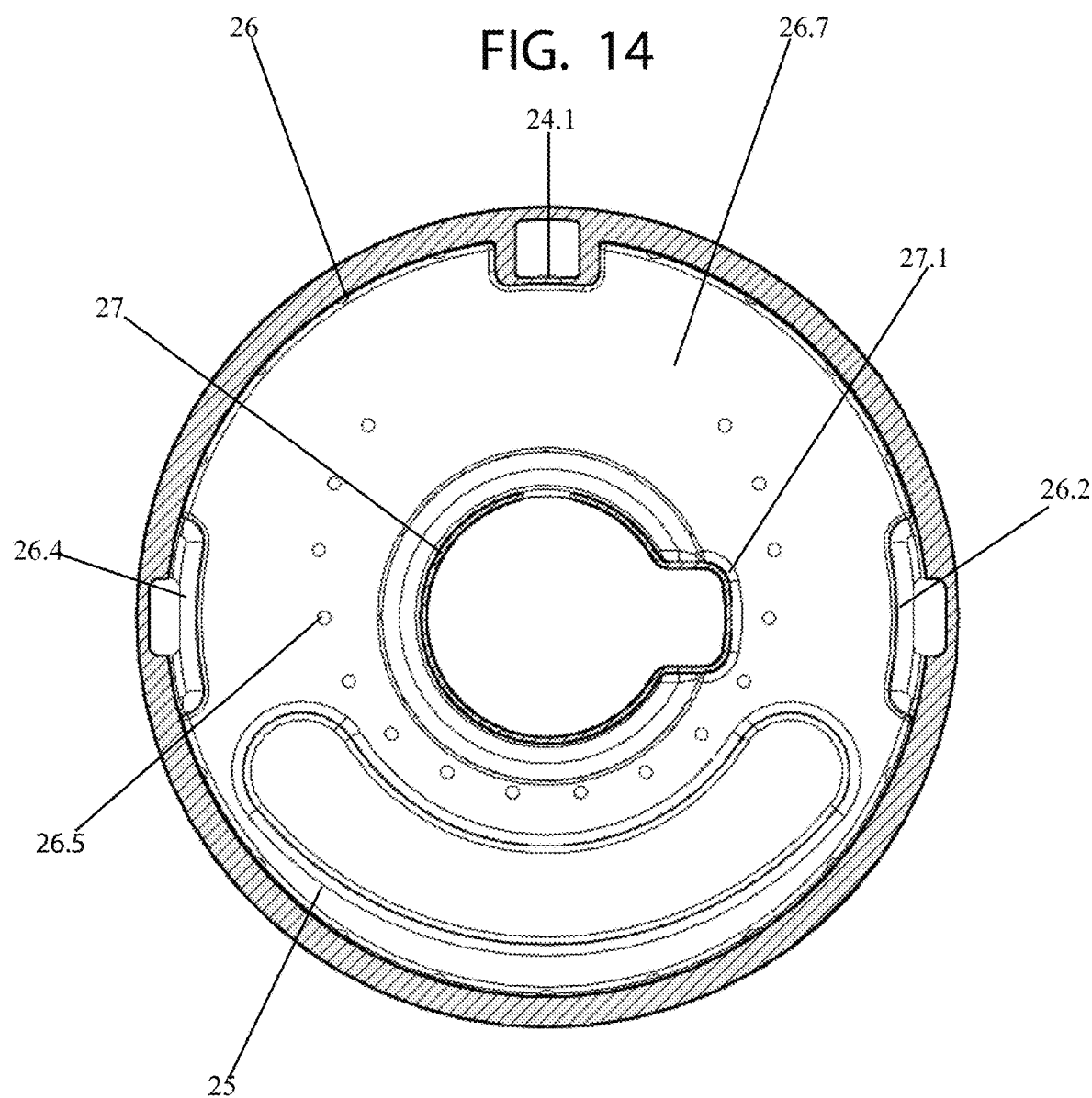

AWE Data Driven Air
Purification Machine
Control

AIR PURIFYING MACHINE AND PROCESS

CROSS REFERENCE TO RELATED APPLICATIONS

This application is a continuation in part application of U.S. patent application Ser. No. 16/231,396 filed on Dec. 22, 2018, (hereinafter the '396 application). The '396 application is a nonprovisional application that claims priority from provisional application 62/711,297 filed on Jul. 27, 2018, and provisional application 62/610,092 filed on Dec. 22, 2017, the disclosures of all of these applications are hereby incorporated herein by reference in their entirety.

BACKGROUND OF THE INVENTION

At least one embodiment comprises an air purifying machine comprising: at least one housing and a plurality of cores disposed in the housing. The cores can be disposed offset from each other to encourage greater interaction with a bioreactive solution.

SUMMARY OF THE INVENTION

At least one embodiment relates to an air purifying machine comprising at least one housing and a plurality of cores wherein each core is disposed in the housing. There is also at least one fan disposed in the housing. In addition, there is at least one pump disposed in the housing, wherein the pump is configured to circulate a fluid inside of the housing.

The cores comprise at least two cores disposed inside of the housing comprising a first core and a second core, wherein the second core is disposed inside of said first core and wherein the second core is not concentric with the first core. The non-concentric nature of the cores creates a compression location at a point where the two cores are disposed closest to each other. This compression location creates a higher pressure location for air flow around the cores. The different size of the openings for air to circulate between the cores creates air turbulence which results in greater interaction between the incoming air and the bioreactive fluid solution inside of the air purification system.

In one embodiment, the second core is disposed adjacent to said first core in the housing such that the second core and the first core together form a venturi effect with the circulating air. In one embodiment the second core has a plurality of holes disposed in at least one side of the core.

In at least one embodiment first core has a larger diameter than said second core. In at least one embodiment there is at least one tray for receiving a fluid. In at least one embodiment the tray comprises a top and a bottom section.

In at least one embodiment the bottom section of the tray has a plurality of holes in it.

In at least one embodiment there is a channel coupled to the pump, wherein said channel extends up from a bottom section of the first and second core to the tray. In at least one embodiment the channel comprises a tube. Along the tube can be at least one valve coupled to the tube, wherein the valve is configured to shut off fluid flow in the tube. Disposed in the housing is at least one microprocessor, wherein said at least one microprocessor is configured to control the pump. In at least one embodiment there is a water inlet and at least one valve, wherein said at least one microprocessor is configured to control said at least one valve to selectively allow water into the container. In at least one embodiment the microprocessor is configured to control least one valve such as a dual solenoid valve to selectively allow water inside of the container.

BRIEF DESCRIPTION OF THE DRAWINGS

Other objects and features of the present invention will become apparent from the following detailed description considered in connection with the accompanying drawings which disclose at least one embodiment of the present invention. It should be understood, however, that the drawings are designed for the purpose of illustration only and not as a definition of the limits of the invention.

In the drawings, wherein similar reference characters denote similar elements throughout the several views:

FIG. 1 is a side view of the air purifying machine;

FIG. 2A is a side view of the top of the air purifying machine;

FIG. 2B is a side view of the air purifying machine with the container cover removed;

FIG. 2C is a side view of the container cover of the air purifying machine;

FIG. 2D is a side view of the device without the container cover and the container;

FIG. 3A is a top view of the container;

FIG. 3B is a top view of the container, the outer core, the inner core and the lower portion of the tray;

FIG. 3C is a top view of the container cover;

FIG. 4A is a side view of the container cover;

FIG. 4B is a side view of the cover and of the outer core;

FIG. 4C is a side view of the container;

FIG. 5A is a side view of the fluid transfer system and the top of the air purifying machine;

FIG. 5B is a side view of the fluid transfer system, the top, the fluid input system, as well as the fluid level system;

FIG. 5C is a bottom view of the view shown in FIG. 5B;

FIG. 5D is another side view of the view shown in FIGS. 5A and 5B;

FIG. 6A is a side view of the container cover;

FIG. 6B is a side view of the outer core;

FIG. 6C is a side view of the container;

FIG. 6D is a side view of the inner core;

FIG. 7 is a side view of the inner core inside of the container;

FIG. 8 is a perspective side cross-sectional view of the container, the outer core and the inner core;

FIG. 9A is a top view of the container, the outer core and the inner core;

FIG. 9B is a bottom view of the inner core;

FIG. 9C is a top view of the container which shows an example of air flow patterns;

FIG. 10 is a top perspective view of the tray;

FIG. 11 is a bottom view of the tray;

FIG. 12A is a side cross-sectional view of the tray;

FIG. 12B is another side cross-sectional view of the tray;

FIG. 13, is a perspective view of the bottom of the tray;

FIG. 14 is a top view of the bottom section of the tray;

FIG. 15A is a schematic block diagram of the electrical components of the air purification device;

FIG. 15B is a network layout of multiple air purification devices;

FIG. 15C is a schematic block diagram of at least one computer;

FIG. 15D is a schematic block diagram of at least one handheld device;

FIG. 16 is a flow chart for a process for running the machine in a night mode;

FIG. 17 is a flow chart for biological reagent dosing;

FIG. 18 is a process for data driven air purification machine control;

FIG. 19 is a process for monitoring air quality.

DETAILED DESCRIPTION OF PREFERRED EMBODIMENTS

FIG. 1 is a side view of the air purifying machine. For example, as shown there is a side view of the device which shows the device/system 10 which includes the top 20, the cover 30 and the outer container 40 with the top 20, the cover 30 and the outer container 40 forming a housing. In at least one embodiment, the housing can be any one of the top 20, the cover 30 and/or the container 40. There is also a bottom 100 which is configured as either a stationary bottom or as a rolling bottom which is configured to rotate as the housing is rotated on an edge.

FIG. 2A is a side view of the top of the air purifying machine wherein this top has a top tray section 22 and a bottom tray section 26. (See FIGS. 11-14 for more detail).

FIG. 2B is a side view of the air purifying machine with the cover removed in this view there is tank 40 with cover 20 disposed on top of this tank. The tank has a bend 42 disposed therein. There is an inlet or circulating tube 124 which is disposed therein. There is also a rotatable bottom 100 which is disposed below tank 40.

Figure 1:
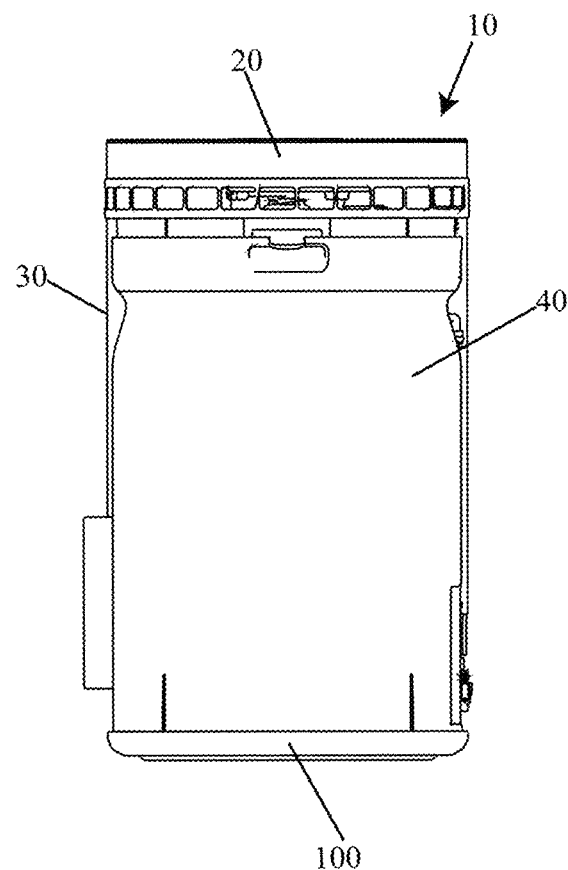
Figure 2A:
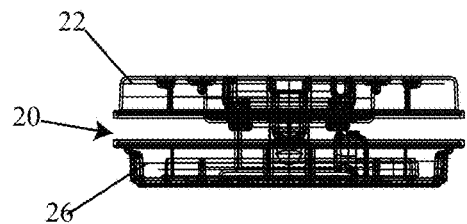
FIG. 2C is a side view of the container cover 30 of the air purifying machine, in this view there is also an indent 32 of the container cover as well.
FIG. 2D is a side view of the device without the cover and the container, this view shows the container cover, as well as the outer core 50 the inner core 60 and the circulating system.
Figure 2B:
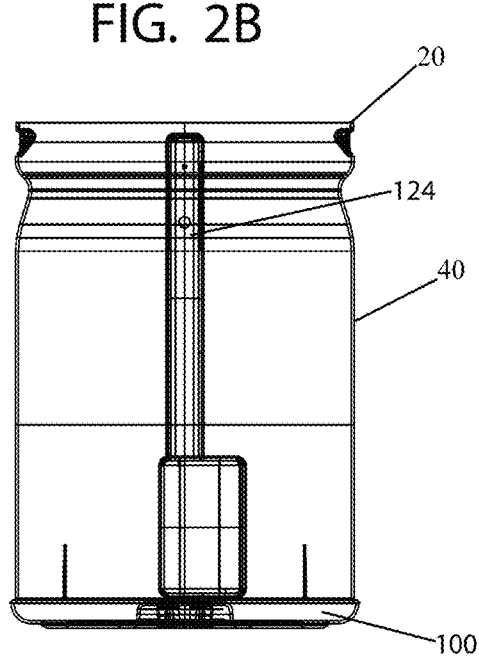
Figure 2C:
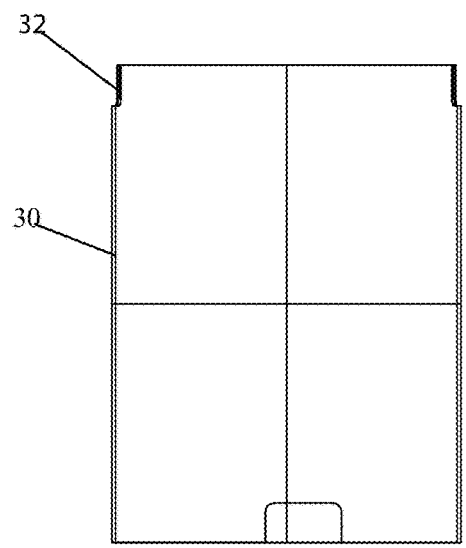
Figure 2D:
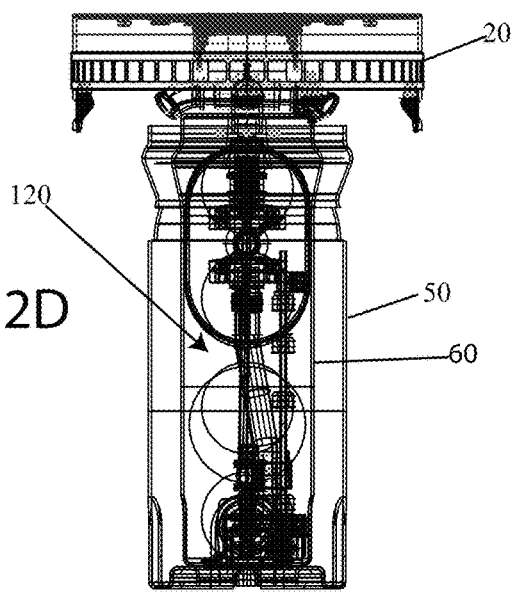
Figure 3A:
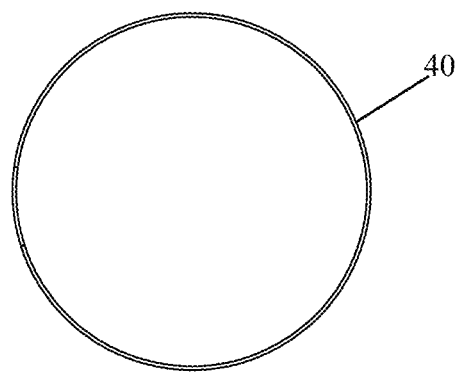
Figure 3B:
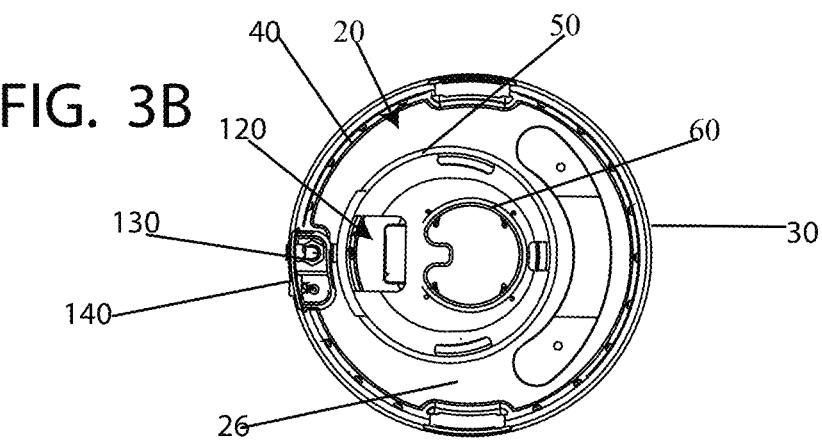
Figure 3C:
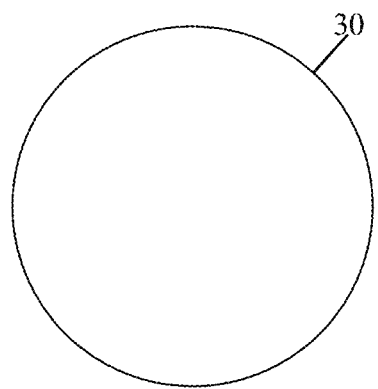

FIG. 3A is a top view of the container 40 while FIG. 3B is a top view of the container, the outer core 50, the inner core 60 and the lower portion of the tray 26. FIG. 3C is a top view of the cover 30 as well.

Figure 4A:
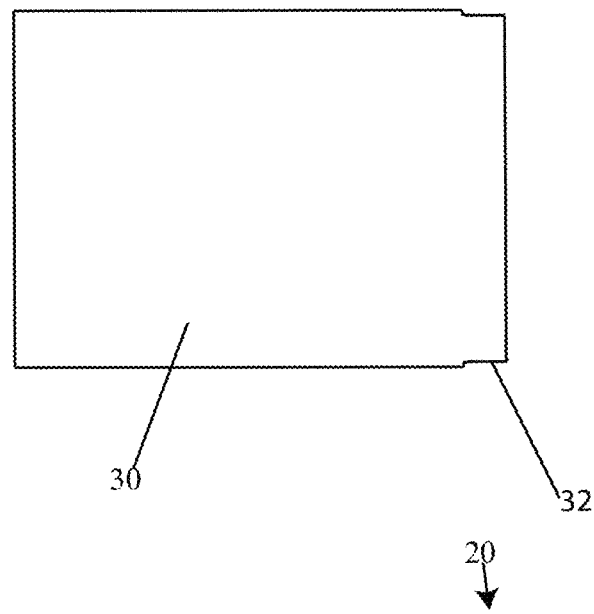
Figure 4B:
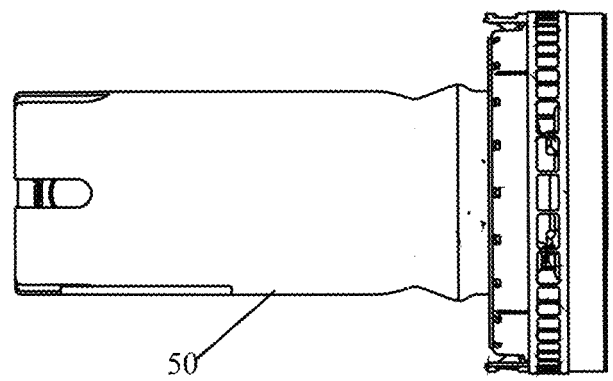
Figure 4C:
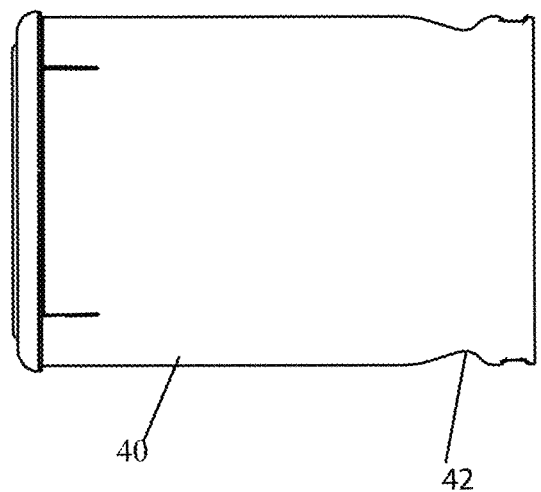

FIG. 4A is a side view of the container cover 30, which has indent 32. FIG. 4B is a side view of the top 20 and of the outer core 50. FIG. 4C is a side view of the container 40 having indent 42.

Figure 5A:
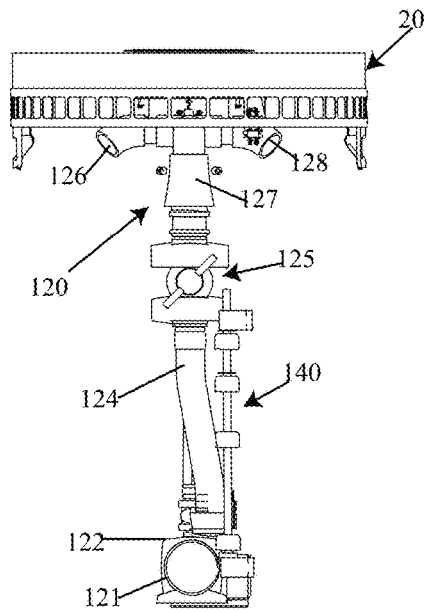

FIG. 5A is a side view of the fluid transfer system and the top of the air purifying machine. In this view there is shown top 20 as well as the circulating assembly 120. At the bottom of the circulating assembly is a pump 121 having a pump inlet 122. Fluid such as water as well as the bioreagent are drawn into the pump inlet 122 and then drawn up to inlet tube 124, through valve 125, through top connector 127 and then out of either first outflow tube 126 or second outflow tube 128. These first and second outflow tubes flow into respective trays of the cover. In addition, positioned adjacent to the circulating assembly 120 is a water level sensor 140 having a plurality of floats.

Figure 5B:
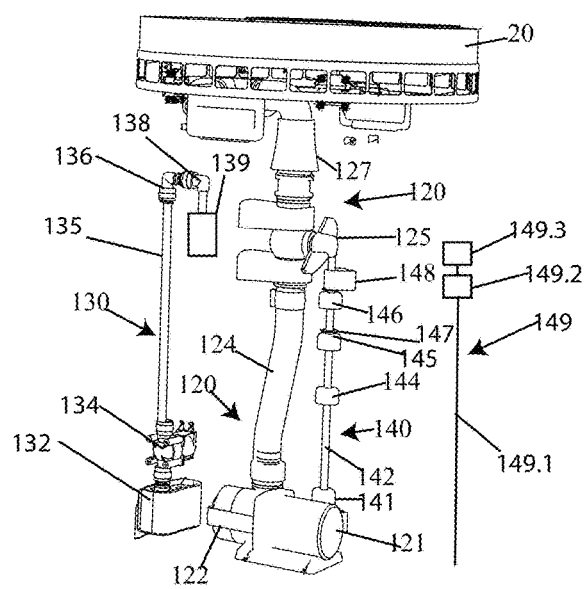

FIG. 5B is a side view of one embodiment of the fluid transfer system, the top, the fluid input system, as well as the fluid level system. For example, there is shown top 20, as well as circulating assembly 120 having top connector 127, as well as valve 125. There is also shown outlet tube 124, as well as pump inlet 122 and pump 121. In addition, there is also a water inlet 130 comprising a water inlet opening 132, at least one or a plurality of solenoid valves (212, 214) inside of a solenoid valve housing 134. In at least one embodiment there are two solenoid valves. These valves selectively open into a feed pipe 135. There are also a plurality of elbows 136 and 138 which then bend the pipe to feed down into a tray.

There is also water level sensor 140 which is shown having a support or pole 142, and a plurality of different float sensors including a first float sensor 141, a second float sensor 144, a third float sensor 145, a fourth float sensor 146 and a stoppers 147 and 148.

There are also at least two optional mechanical floats or sensors which are configured for automatic shutoff of the water intake in case the float sensor system 140 fails. For example, there is a first mechanical fluid level sensor such as a mechanical float, 139 which includes a valve and is configured to automatically mechanically shut off the water opening into the container 40 from water feed pipe 135. In addition, there is also an additional mechanical float sensor comprising mechanical floats as shown as electro mechanical float 149. The electro mechanical float 149 includes a post or support 149.1 as well as two separate mechanical floats 149.2 and 149.3. The first float 149.3 is a mechanical fail-safe float, wherein when the fluid is too high floats up and cuts off power to the solenoids such as solenoids 212, and 214 (see FIG. 15A) inside of solenoid valve housing 134. Second float 149.2 is configured to sound an alarm when the fluid level is too high such as alarm 207 which can be either incorporated into the housing or remote from the housing and in communication with the controller in either a wired or wireless manner.

Figure 5C:
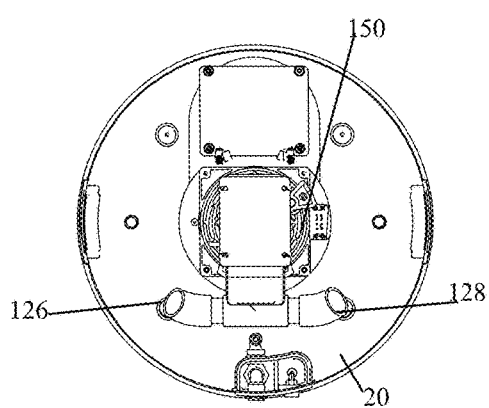

FIG. 5C is a bottom view of the view shown in FIG. 5B. This view shows fan 150 which is situated in the top cover 20 and is positioned adjacent to the first and second outflow tubes 126 and 128.

Figure 5D:
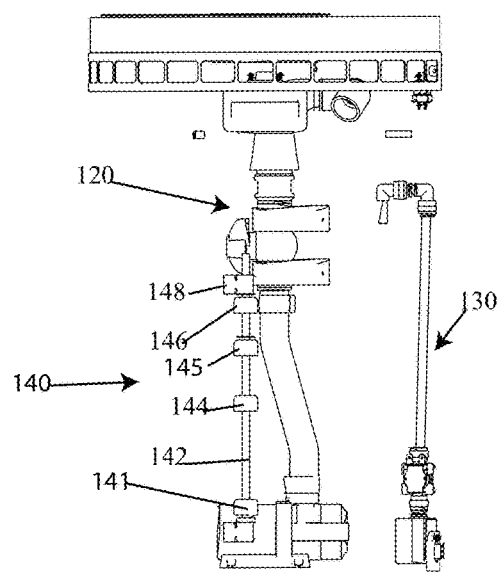

FIG. 5D is another side view of the view shown in FIGS. 5A and 5B. In this view there is shown circulating assembly as well as the water level sensor 140 including pole 142, and float sensors 141, 144, 145, and 146 as well as stopper 148. In addition, this view also shown water inlet 130 as well.

Figure 6A:
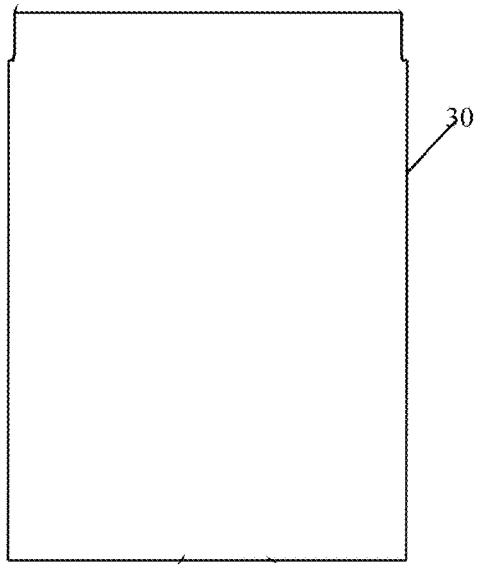
Figure 6B:
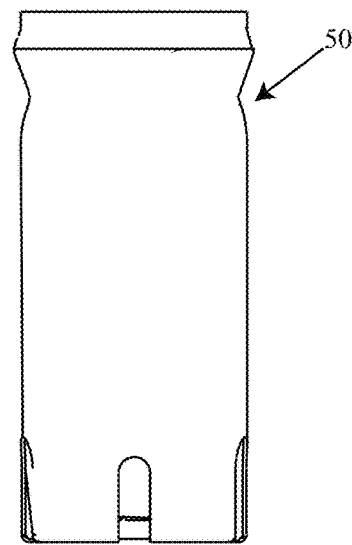
Figure 6C:
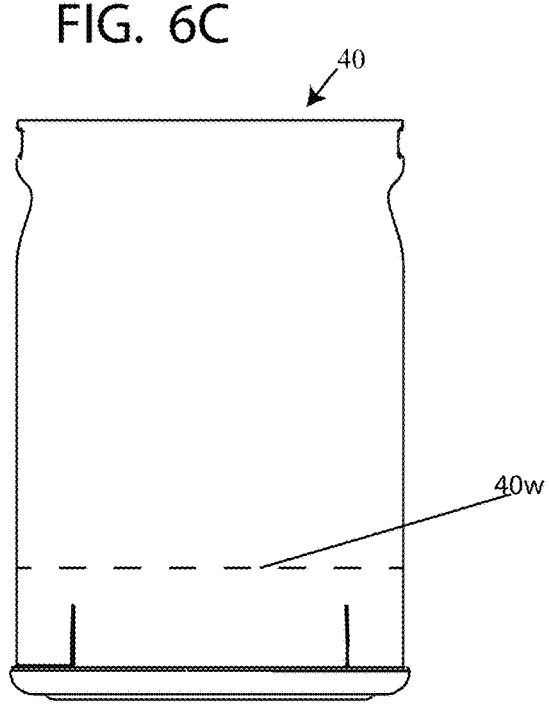
Figure 6D:
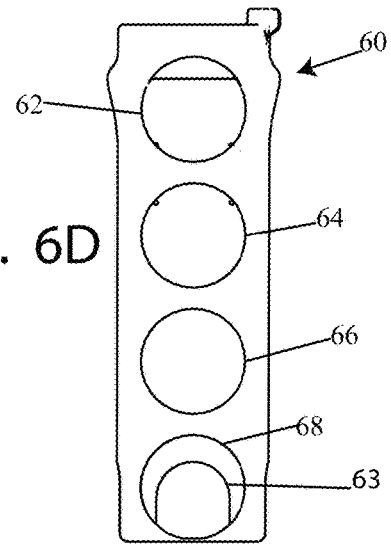

FIG. 6A is a side view of the cover 30, while FIG. 6B is a side view of the outer core 50. FIG. 6C is a side view of the container 40. In this view, container shows an approximate fill level 40w for the solution of bioreactive solution which includes a bioreactive agent mixed with water. This bioreactive solution is then pumped up to a top cover 20 so that this fluid then spills down an inner wall of outer core 50 and both the inner and outer walls of inner core 60. FIG. 6D is a side view of the inner core 60. As shown in this view inner core has a plurality of different openings which in at least one embodiment is a plurality of circular openings comprising openings 62, 64, 66, and 68. In addition another opening 61 is positioned opposite opening 68 as well.

Figure 7:
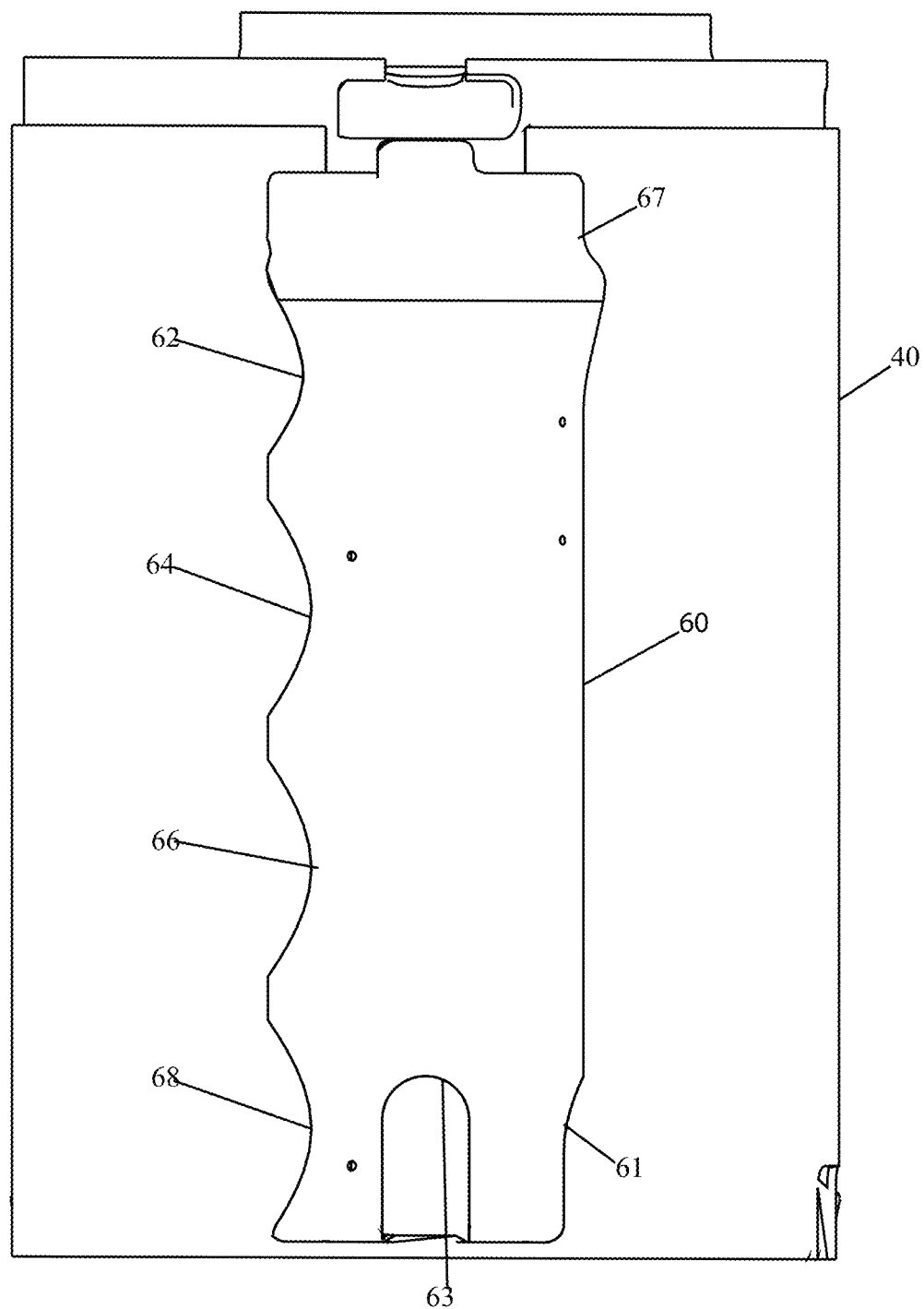

FIG. 7 is a side view of the inner core inside of the container 40. For example, inner core 60 is shown with openings 62, 64, 66, and 68 as well as a side opening 63, and an opposite opening 61.

Figure 8:
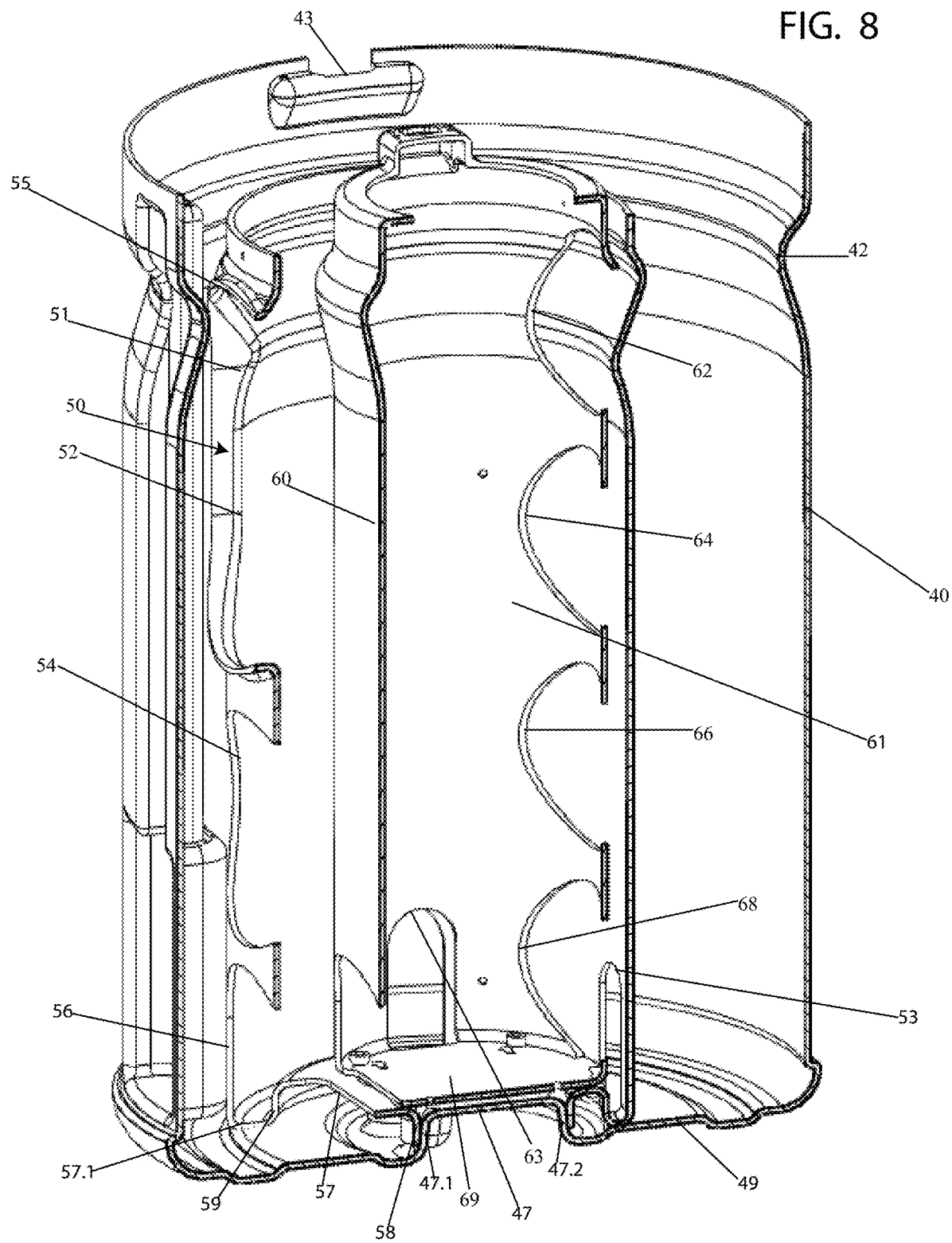

FIG. 8 is a perspective side cross-sectional view of the container, the outer core and the inner core. In this view, there is shown container 40, as well as outer core 50, and inner core 60. With container 40, there is shown bend 42 as well as indent 43. Container 40 includes a raised bottom section 47 which is raised up by vertical bottom sections 47.1 and 47.2. There is shown an outer core 50 which has a body section 51, a first opening 52, a second opening 54, and a third opening 56. There is also a notch 55 disposed towards a top region. These openings 52, 54, 56 are disposed opposite the openings on the inner core 60. There is also an additional opening 53, which is disposed opposite openings 52, 54, and 56. In addition, in a bottom region there is an elevated bottom surface 57, as well as substantially vertically raised surfaces which rise from a first bottom section 57.1 to upper bottom section 57. This outer core also has substantially vertical sections 58 and 59 which are used to join first bottom section 57.1 and upper bottom section 57.

Inner core 60 includes a plurality of different openings as well. For example, there is a shell portion 61 as well as a plurality of openings, comprising a first upper opening 62, a second opening 64, a third opening 66, wherein these openings are disposed opposite openings 52, 54, and 56. In addition, inner core 60 also includes opening 63 which is disposed adjacent to openings 62, 64, 66 and 68.1. There is also an oppositely spaced opening 68.2. While these openings are shown as semi-circular, these openings are actually circular or substantially oval, however these openings can be of any suitable shape as well.

Figure 9A:
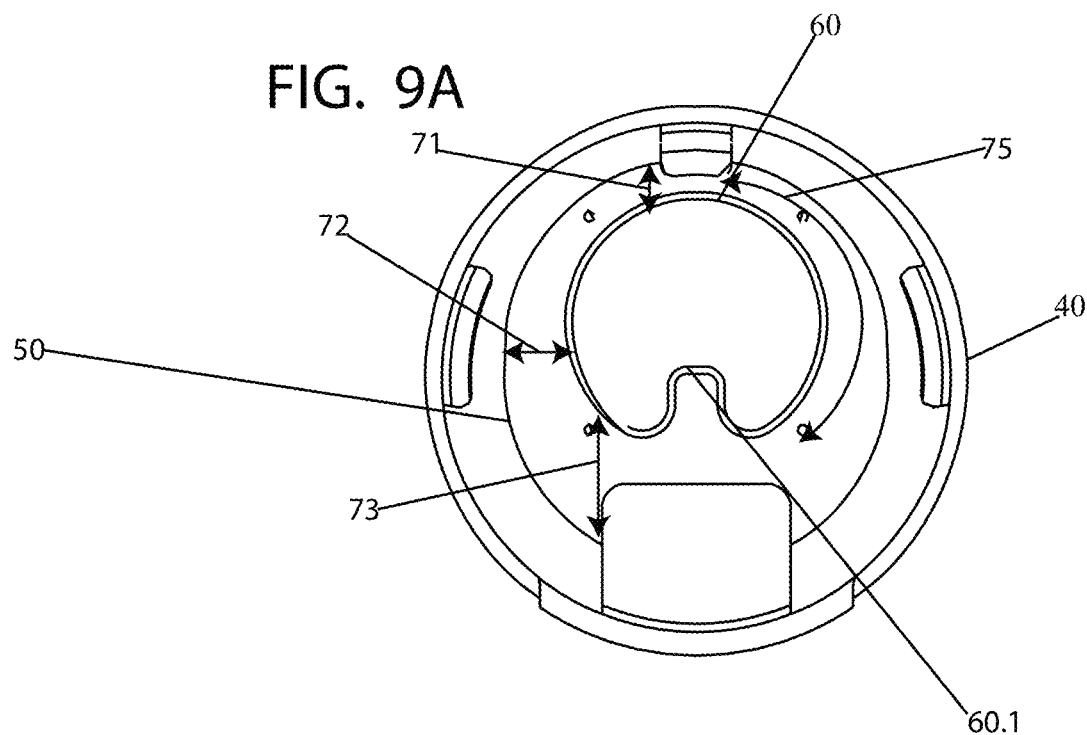

FIG. 9A is a top view of the container 40, the outer core 50 and the inner core 60. As shown in the top view, there is shown an indent 60.1 which bends inward and which is used to allow the inlet tube 124 to extend upward therein. As shown in this view, outer core 50 is shown extending around inner core 60. In addition, there is shown the different distances shown by arrows 71, 72, and 73. For example, as shown the fluid flow of gaseous material such as air is round the inner core and between the inner core 60 and the outer core 50. As the fluid flows around the inner core 60, the air is compressed in the region 71, and the opening is gradually larger in region 72, and even larger in region 73. The narrowing and then eventual enlargement of the opening creates a venturi effect which further promotes interaction between the air and the bioreagent solution. The different distances such as distances 71, 72, and 73, are configured to create turbulence which results in increased interactions between outer core 50 and inner core 60.

Figure 9B:
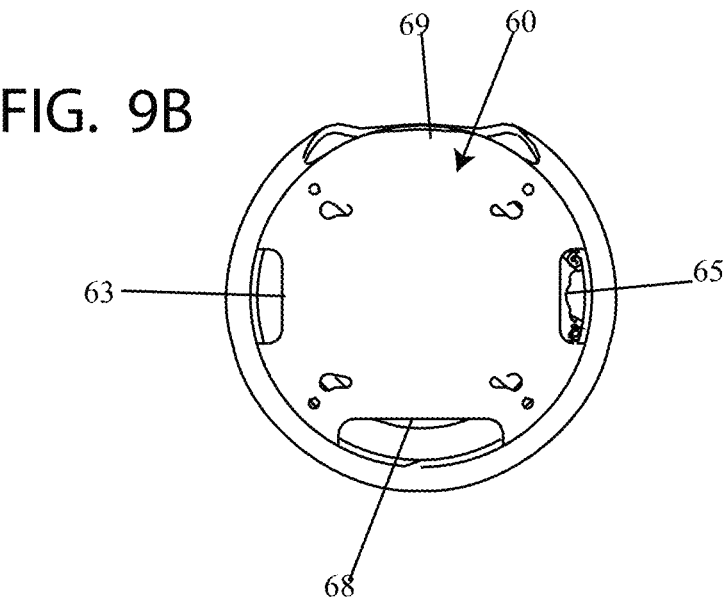

FIG. 9B is a bottom view of the inner core 60. This view shows a bottom plate 69, which has openings 63, 65, and 68.1 and 68.2.

Figure 9C:
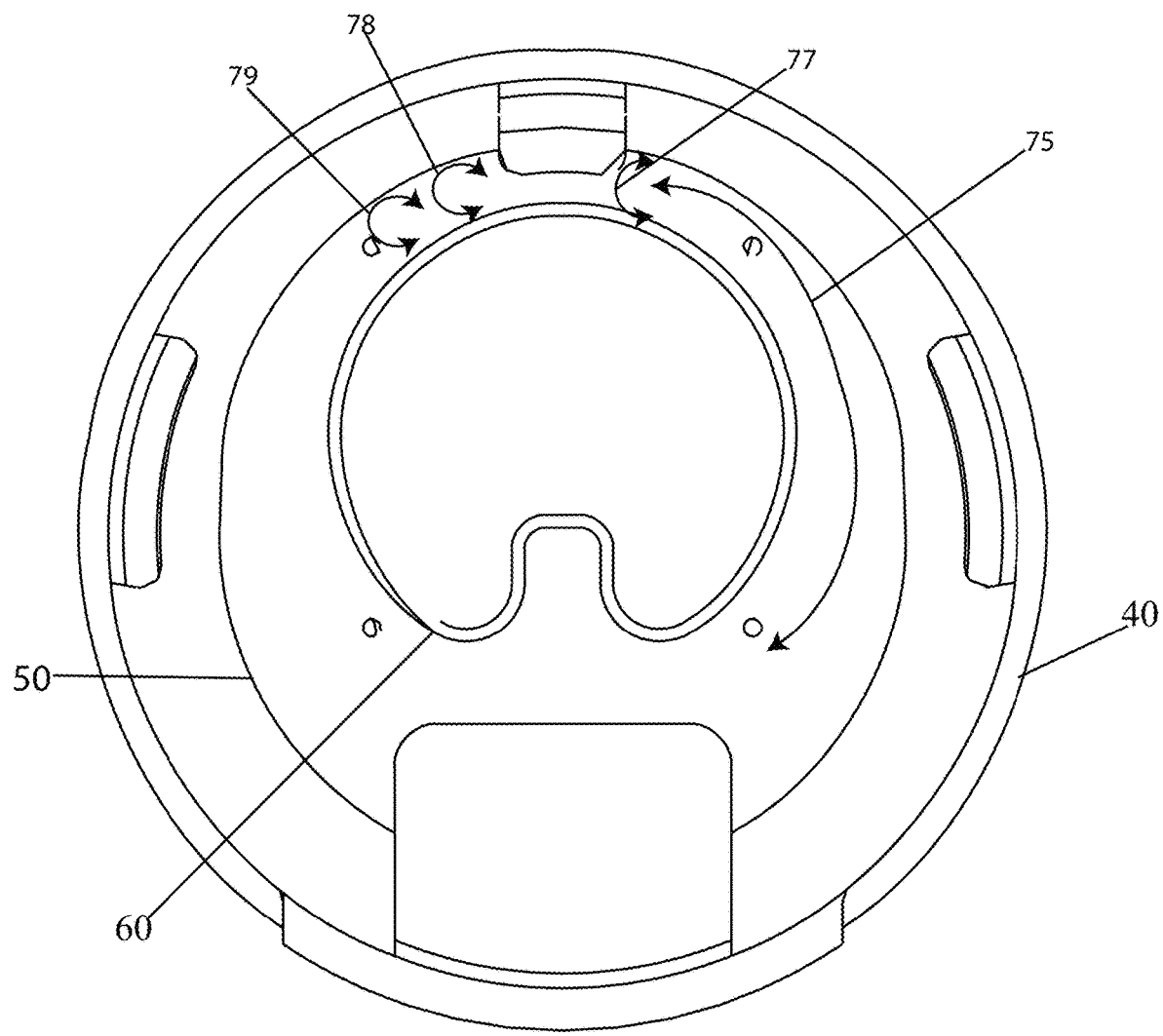

FIG. 9C is a top view of the container which shows an example of air flow patterns. With this design, there is shown container 40, outer core 50 and inner core 60. In the region where inner core 60 is disposed substantially closest to the outer core 50, this creates a more narrowed opening which creates air turbulence as shown by way of arrows 77, 78 and 79. Ultimately this increasing narrowing and then expansion of volume adjacent to the narrowed section, creates a venturi effect for the travel of air through this narrowed region creating different more interactive air currents. These more turbulent air currents in the narrowed region create increased interaction. In addition, the increase in air pressure in the region where the volume or space is narrowed, this results in a short-term rise in pressure in this region also fostering greater interaction between the air and the bioreactive solution.

Figure 10:
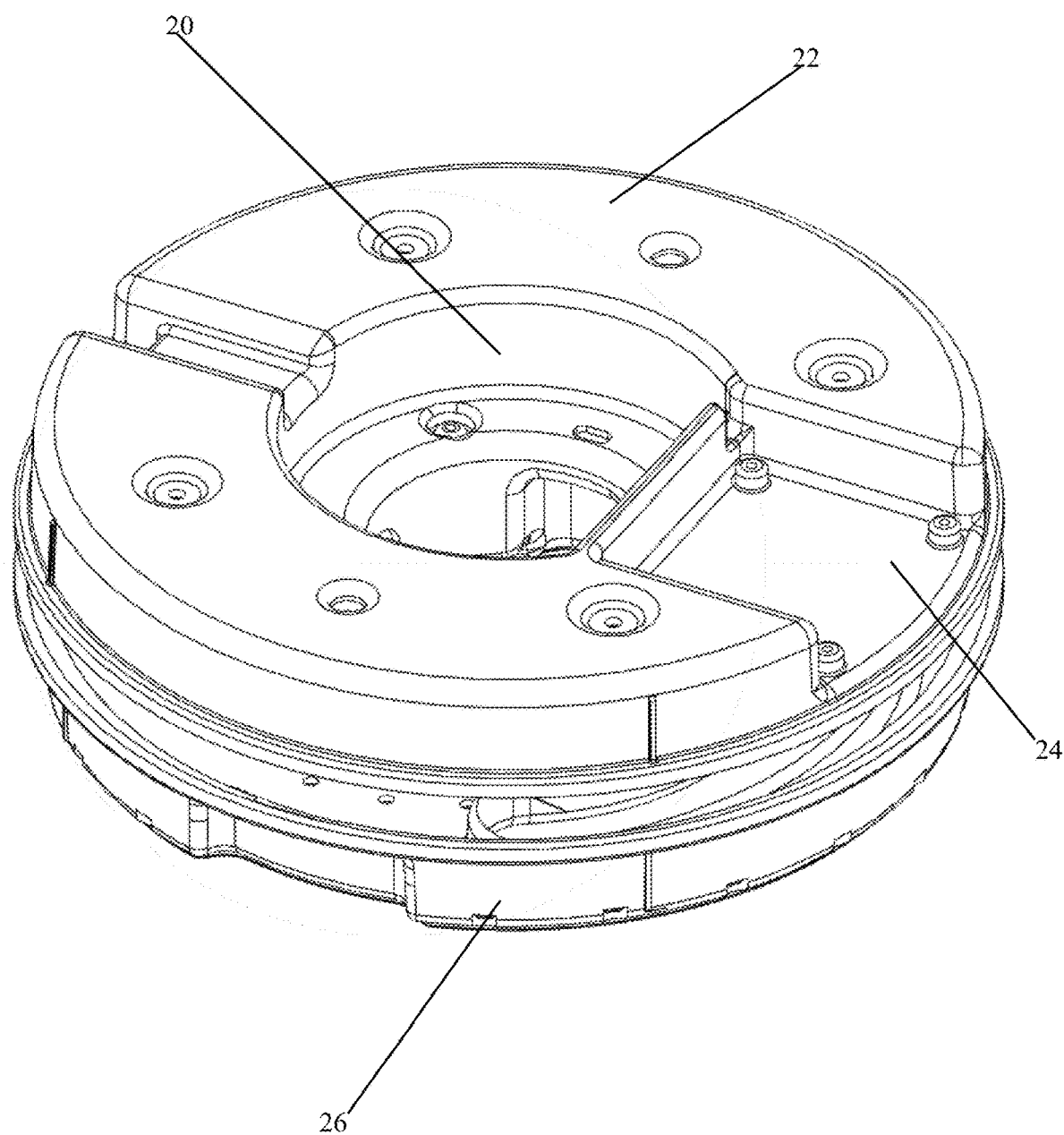

FIG. 10 is a top perspective view of the tray or cover 20 which includes a top tray 22 and a bottom tray 26. There is also an indented portion 24 which is indented into top tray 22.

Figure 11:
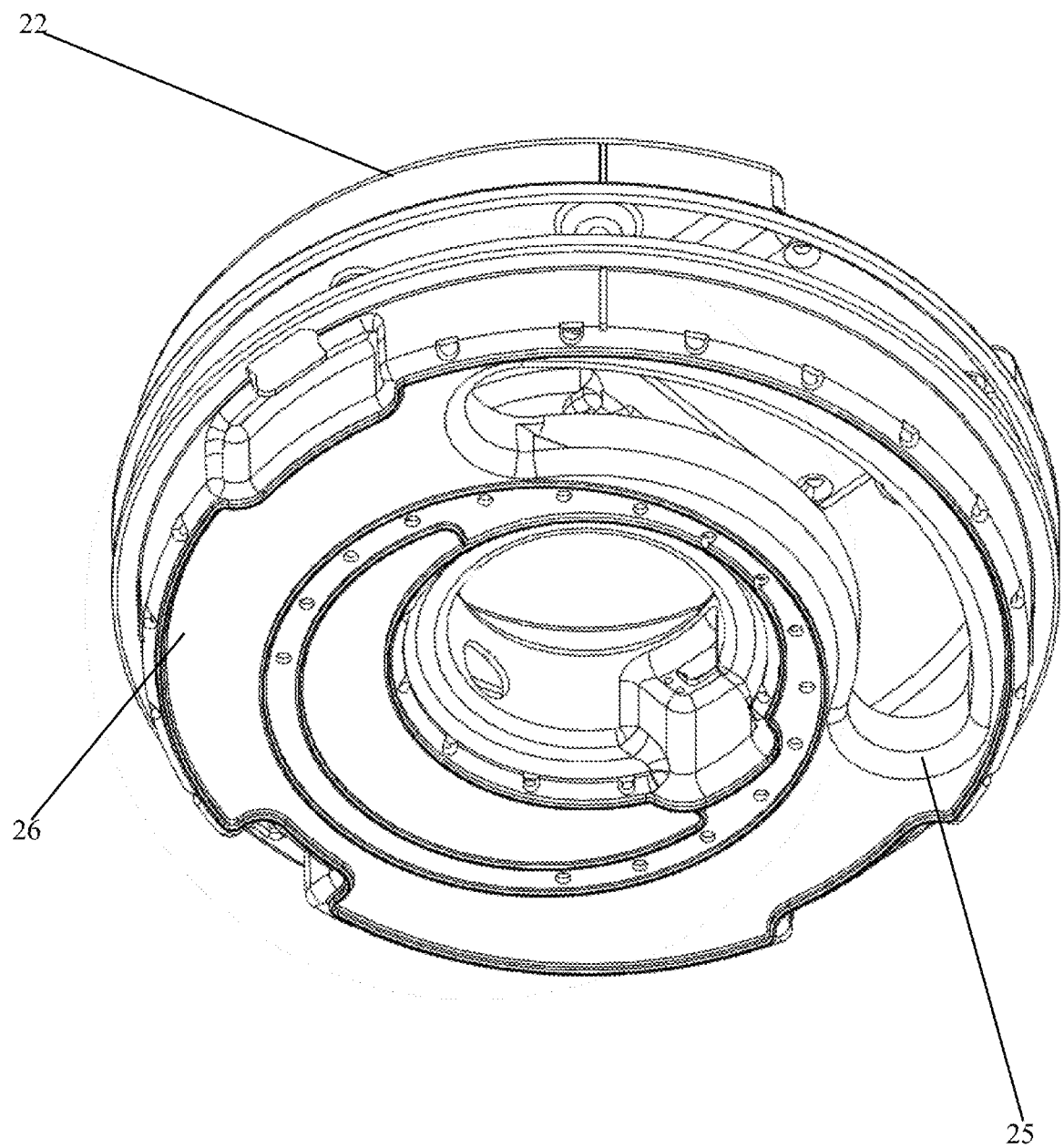

As shown in FIG. 11, top tray 22 is shown coupled to bottom tray 26 with an opening 25 shown in bottom tray 26. Inlet tube 124 (See FIGS. 5A-5C) is configured to feed fluid such as water and proprietary biological reagent mixed with the water into bottom tray 26.

Figure 12A:
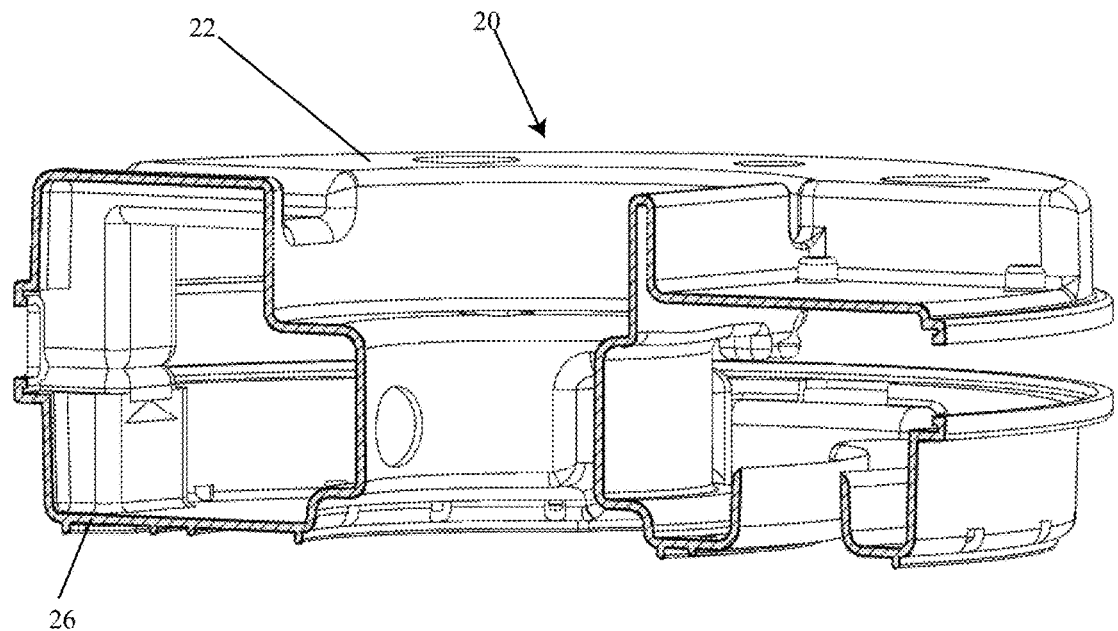

FIG. 12A is a side cross-sectional view of the tray which shows top tray 22 and bottom tray 26 of top assembly 20.

Figure 12B:
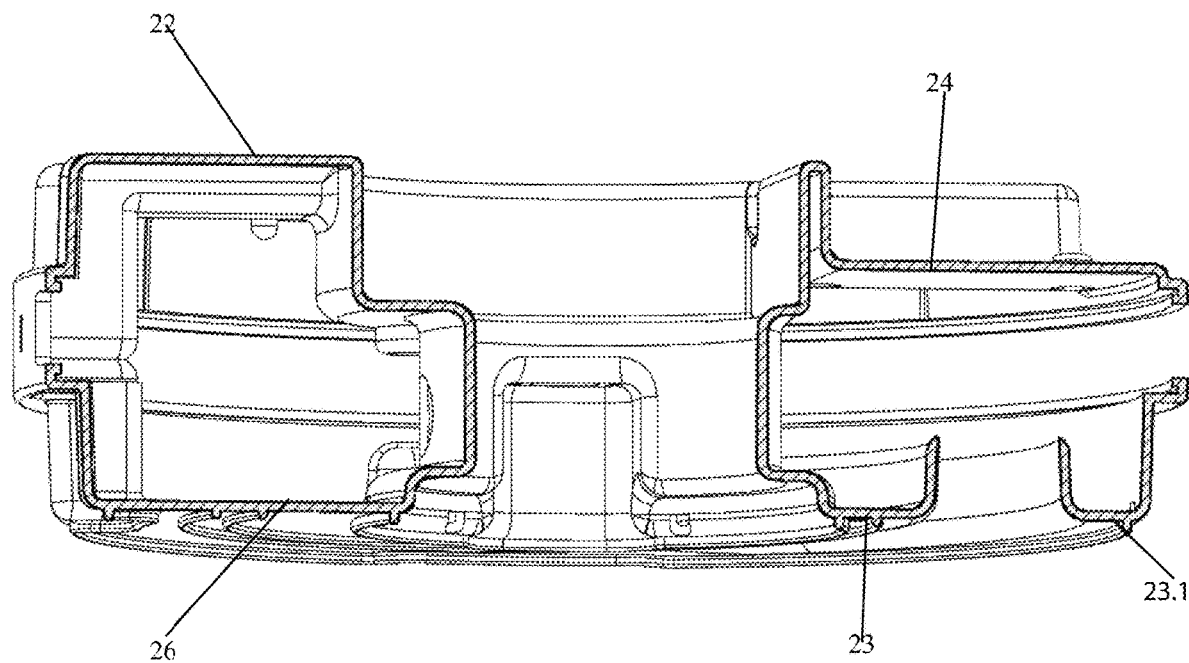

FIG. 12B is another side cross-sectional view of the top assembly 20 including top tray 22 and bottom tray 26. With this view there is shown track 23 which is configured to receive inner core 60, and outer rim 23.1 which is configured to receive outer core 50.

Figure 13:
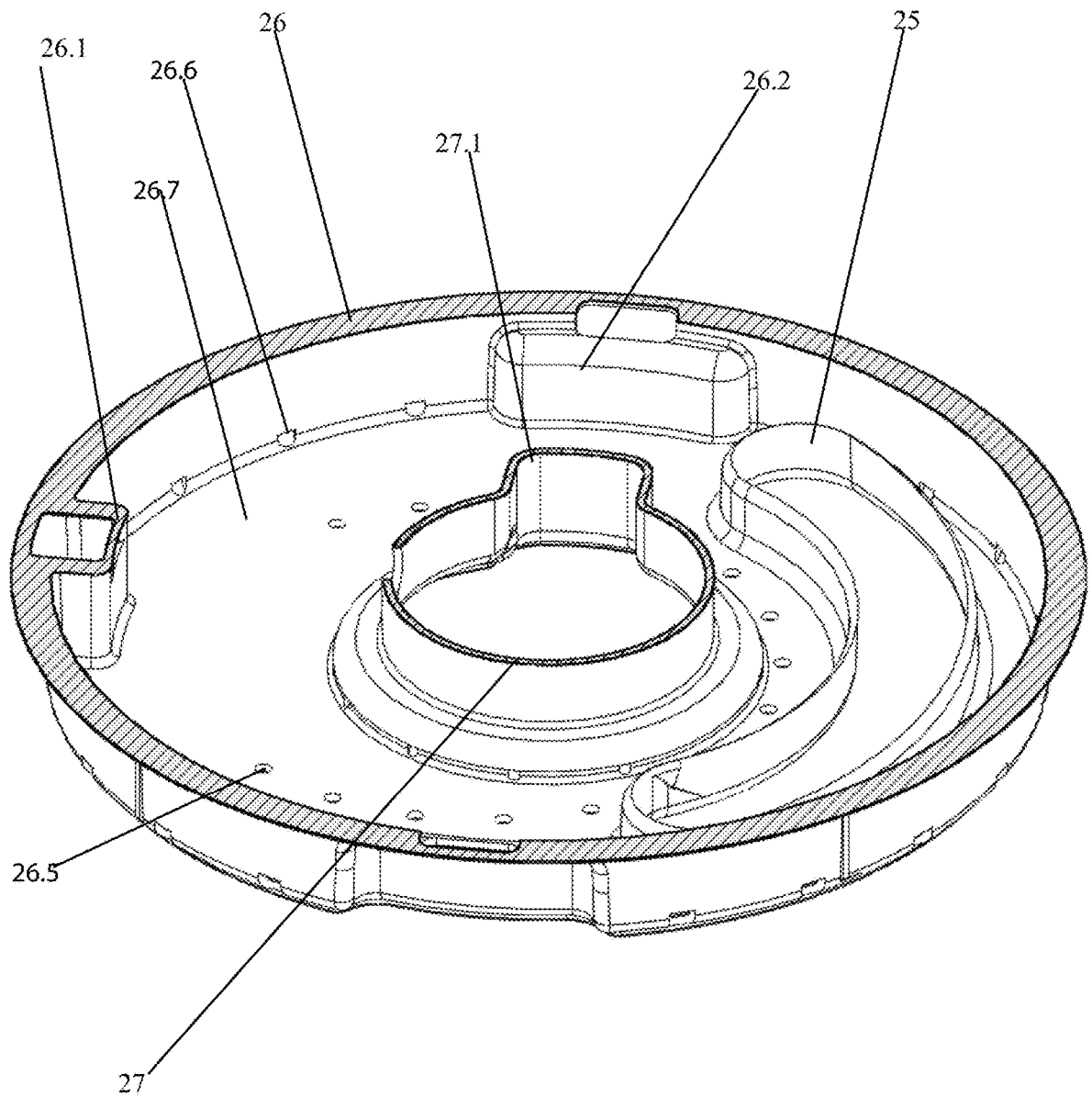

FIGS. 13 and 14, are a perspective view of the bottom of the tray 26 and a top view of the bottom tray 26. In both of these drawings there is shown an inner wall 27, as well as an indented portion 27.1 of inner wall 27. There is also another wall 25 which extends up from a bottom surface 26.7. Bottom tray 26 includes a first indent 26.1 as well as a second indent 26.2. Bottom tray 26 includes a plurality of holes 26.5 forming an inner ring of holes for feeding into the sides of inner core 60. In addition, bottom tray 26 also includes a plurality of holes 26.6 which are configured to feed into the top of outer core 50. FIG. 14 also shows an oppositely spaced indent 26.4 of the bottom section of the tray 26.

Figure 15A:
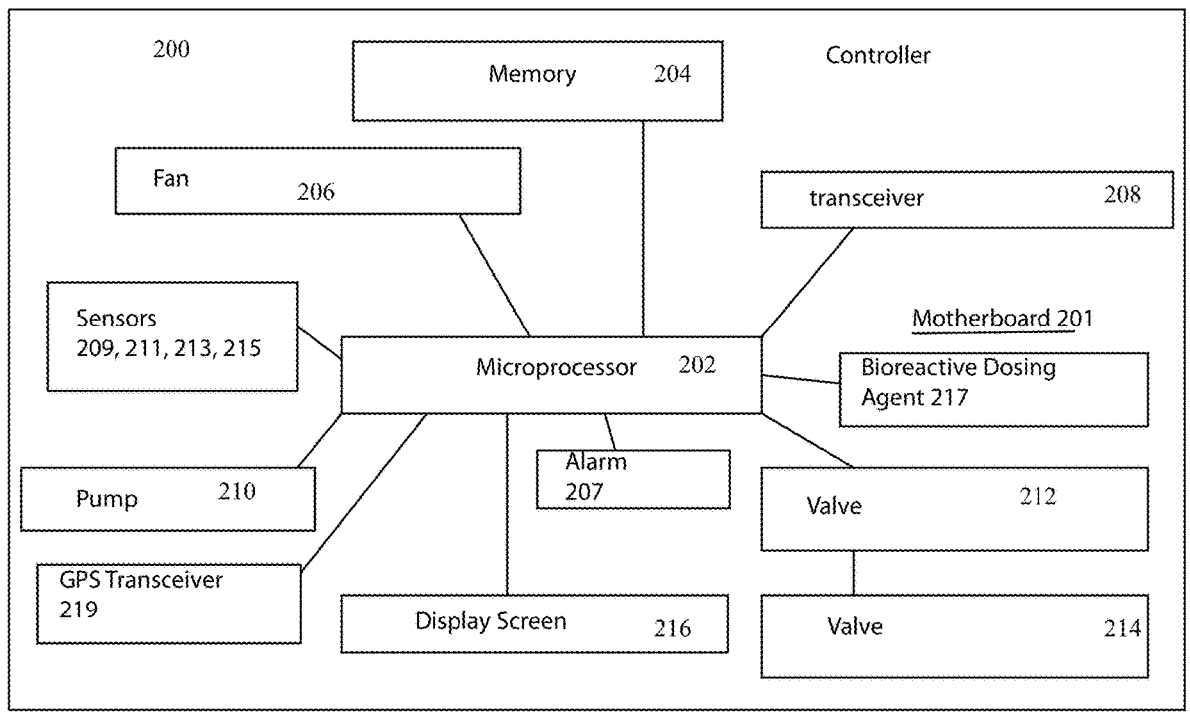

FIG. 15A is a schematic block diagram of the electrical components of the air purification device. With this view there is shown a controller system 200 including a motherboard 201. Coupled to motherboard 200 is microprocessor 202. Microprocessor 202 is also in communication with memory 204. In addition, fan 206 (which can also be fan 150) and transceiver 208 are also in communication with microprocessor 202. In addition, pump 210 (which can also be pump 121) is also in communication with microprocessor 202. In addition, dual solenoid valves 212, and 214 are in communication with microprocessor 202 as well. Solenoid valves 212 and 214 are disposed inside of the solenoid valve housing 134 which can house both of these solenoid valves. There is also a display screen 216 which is a touch sensitive display screen that sits on a top portion of the housing which is in communication with microprocessor 202. In addition, microprocessor is configured to be in communication with a plurality of sensors such as any one of sensors 209, 211, 213, and 215. Sensor 209 is a VOC or volatile organic compound sensor, sensor 211 is a particulate sensor. Sensor 213 is a humidity sensor, and sensor 215 can be any other suitable type sensor. In addition, there is also a GPS transceiver 219 which is configured to relay the location of the controller 200. The GPS transceiver allows for a server (See FIG. 15B) to locate each of these controllers and to determine the air quality in these locations. Furthermore, microprocessor 202 is also in communication with an alarm 207 so as to selectively sound an alarm when the device needs either repair, additional dosing of bioreactive agent, or other type of maintenance. This alarm can be either incorporated into the housing or remote from the housing and either in wired or wireless communication with controller 200 including microprocessor 202. Furthermore, there is an optional bioreactive dosing agent 217 which is configured upon communication from microprocessor 202 to add additional bioreactive agent through an automatic feed into the bioreactive solution. This feeding can be triggered based upon a set of predetermined values stored in memory 204.

Figure 15B:
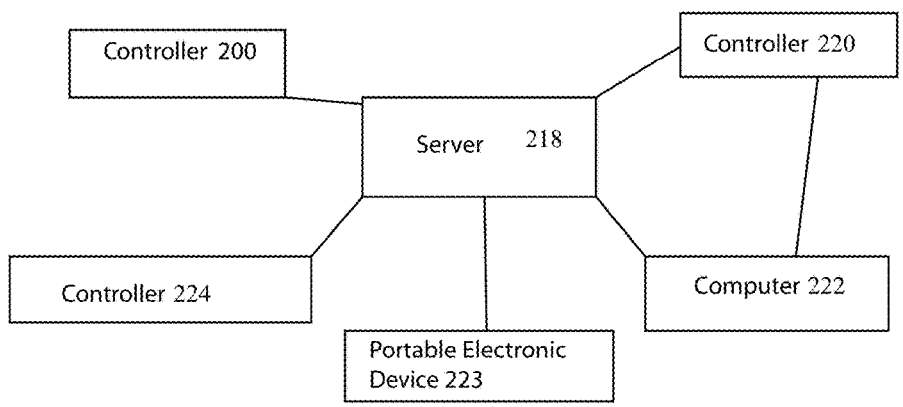

FIG. 15B is a network layout of multiple air purification devices which can include a server 218 as well as multiple different controllers such as controller 200, as well as controller 220 and controller 224. There can also be a computer such as computer 222 in communication with server 218 as well as a portable electronic device such as a smartphone 223 in communication with server 218. With this network a computer such as computer 222 can control the air purification devices through communicating with any one of the air purification devices by communicating through a computer network through either WiFi, Bluetooth, or cellular communication. For example, the computer 222, can communicate directly with controller 220 such as through Bluetooth communication. Alternatively, computer 222 can communicate through a computer network such as through server 218 and then with controller 220. Computer 222 can also communicate with a remotely located controller such as controller 200 by communicating through server 218 as well. In addition, portable electronic device 223 is also in communication with controller 224 such as direct communication through Bluetooth or some other form of direct communication. Alternatively, portable electronic device 223 can be in communication with a remotely located controller 200 such as through server 218.

Microprocessor 202 is configured to perform a series of steps in a program. The following programs can be installed in the memory 204 and then run by processor 202.

Figure 15C:
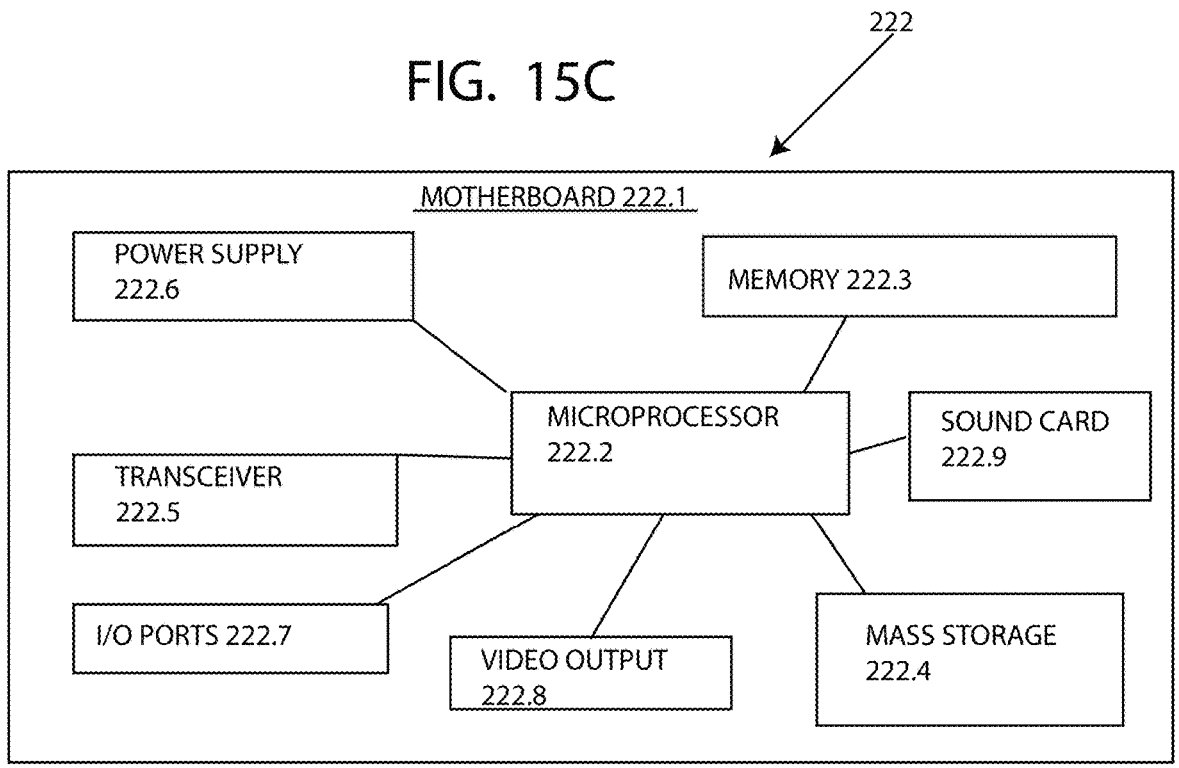

FIG. 15C is a schematic block diagram of a computer such as computer 222 that is used in the computer network shown in FIG. 15B. For example there is shown a motherboard 222.1, which has connected to it a microprocessor 222.2, a memory 222.3 which can be a flash memory or RAM, a mass storage or hard drive 222.4, a transceiver such as ethernet or WIFI 222.5, a power supply 222.6, I/O ports 222.7, a video screen or output 222.8, a sound card 222.9. With this design, a program which is stored in mass storage 222.4 and/or memory 222.3 is then loaded into microprocessor 222.2 which then is programmed to run any suitable software such as a set of processes such as disclosed below for controlling a controller such as controller 200.

Figure 15D:
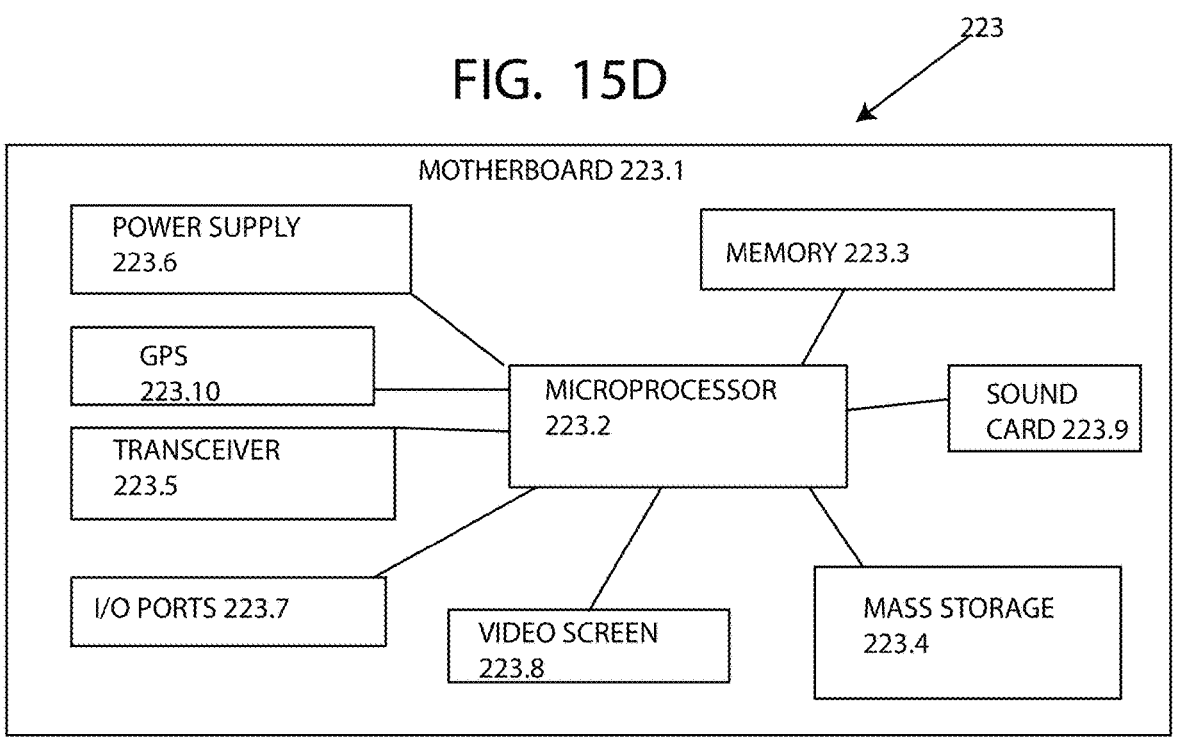

In addition, as shown in FIG. 15D there is a portable electronic device such as a smartphone 223 shown which includes a motherboard 223.1, a microprocessor 223.2, a memory 223.3, a mass storage device 223.4 or drive for storage, this storage drive can also double as working memory by using a memory chip which supports both RAM and ROM. There is also a transceiver 223.5 which can include any one of a SIM card, CDMA card, a Wi-Fi, Bluetooth transceiver or any other suitable wireless or wired transceiver for input and output of communications. There is also a power supply 223.6 which is essentially a battery supply, at least one I/O port 223.7 which can be used for connecting in a wired manner to another computer or power charger. There is also a video screen 223.8, which displays the output of the microprocessor 223.2, and a sound card 223.9 which includes both input (microphone) and output speaker for the portable electronic device. There is also a GPS transceiver so that the device can interact with GPS satellites and obtain GPS coordinates of the device. All of these components are connected through the motherboard 223.1 and are configured to communicate with at least one server such as server 218 and/or at least one controller such as any one of controllers 200 220, and or 224. With this portable electronic device, the microprocessor 223.2 can be fed at least one set of instructions or program from memory 223.3. These set of instructions can be used to control any one of the controllers such as controller 200, controller 220, and or controller 224 from the portable electronic device 223.

Figure 16:
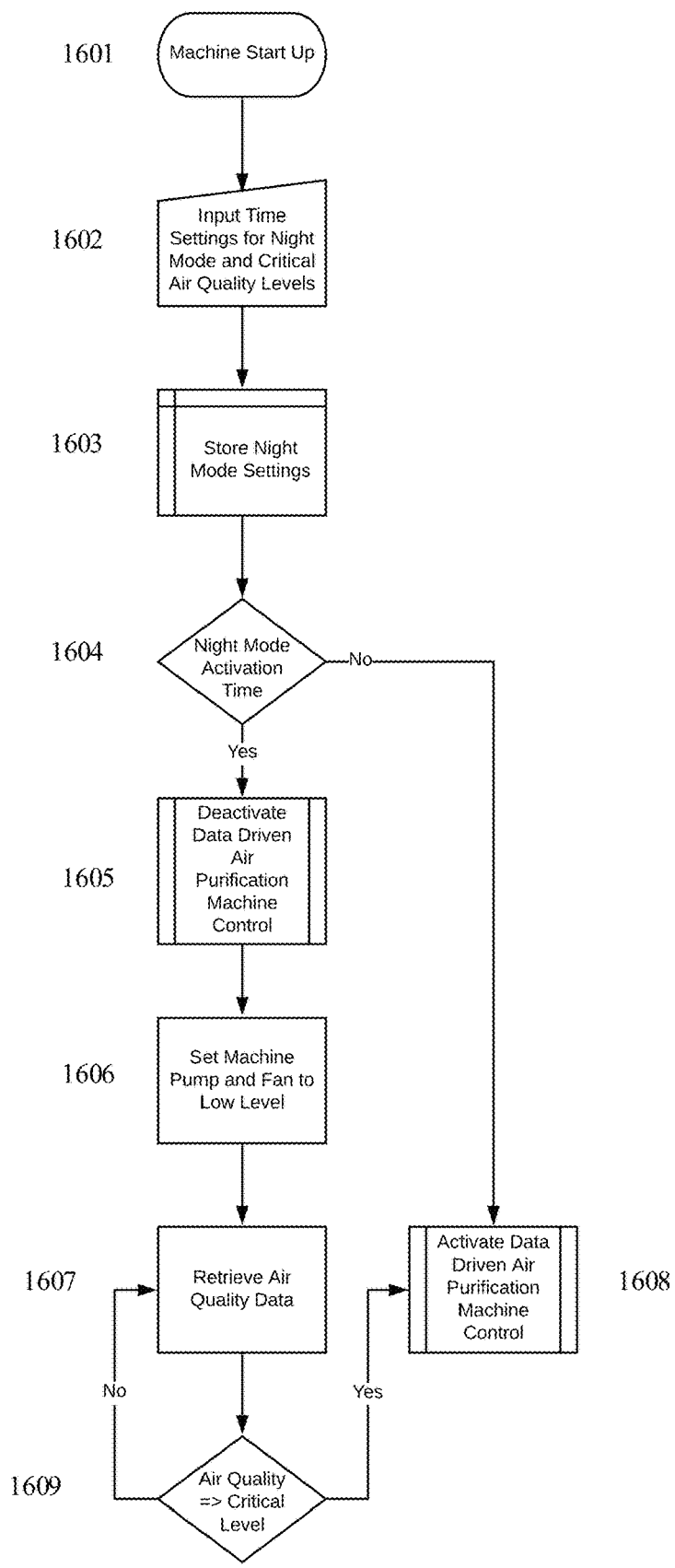

FIG. 16 is a flow chart for a process for running the machine in a night mode. With night mode, the machine operates on a quieter process which is configured to keep noise to a minimum. For example, the process starts in step 1601 wherein the machine starts up and is turned on. The start up and turn on process can be through a user pushing on a screen such as screen 216. Display screen can be in the form of a capacitive touch screen or any other usable screen as well. Alternatively, the user can push a start button on the device itself or the user can start the device remotely through a user's computer such as computer 222 or through the portable electronic device such as portable electronic device 223. Next, the user can input the time settings for night mode and critical quality controls. The means for inputting this information can also be achieved either through the screen 216, or through the computer 222, or through the portable electronic device 223. Next, the night mode settings can be stored in a memory such as memory 204. In step 1604 at the time that was pre-set, there is a night mode activation time. If it is not the night mode time, the process can continue until step 1608 wherein the system can activate data driven air purification machine control. Alternatively, if it is night mode time, the system can proceed until step 1605 wherein the system can deactivate data driven air purification machine control. This data driven air purification machine control is configured to react to the conditions surrounding the machine during the day time. Thus, if there is present a greater number of particulates or impurities, then the system proceeds forward to react to the particulates in the surrounding atmosphere. However, in night mode, the system proceeds to step 1606 wherein the system sets the machine pump and fan to a low level. Next, in step 1607, the system retrieves air quality data. This retrieval of air quality data can be through any one of the sensor(s) such as VOC sensor 209, particulate sensor 211, humidity sensor 213, and/or any other type of suitable air quality sensor 215.

Next, in step 1609 the system can determine if the air quality is greater than or equal to a critical level of particulates, VOC's or any other pollutant to be monitored. If the air quality is low i.e. the amounts of VOC's and/or particulates, and/or natural pollutants such as pollen are greater than a critical level, the process can proceed to step 1608 wherein the system can activate data driven air purification machine control and continue to operate the device until the air quality is below a critical level. The critical level is to be distinguished from an ordinary optimal level in that a normal optimal level is one that would trigger the device to signal the fan to operate faster during a day mode (non-night mode).

Figure 17:
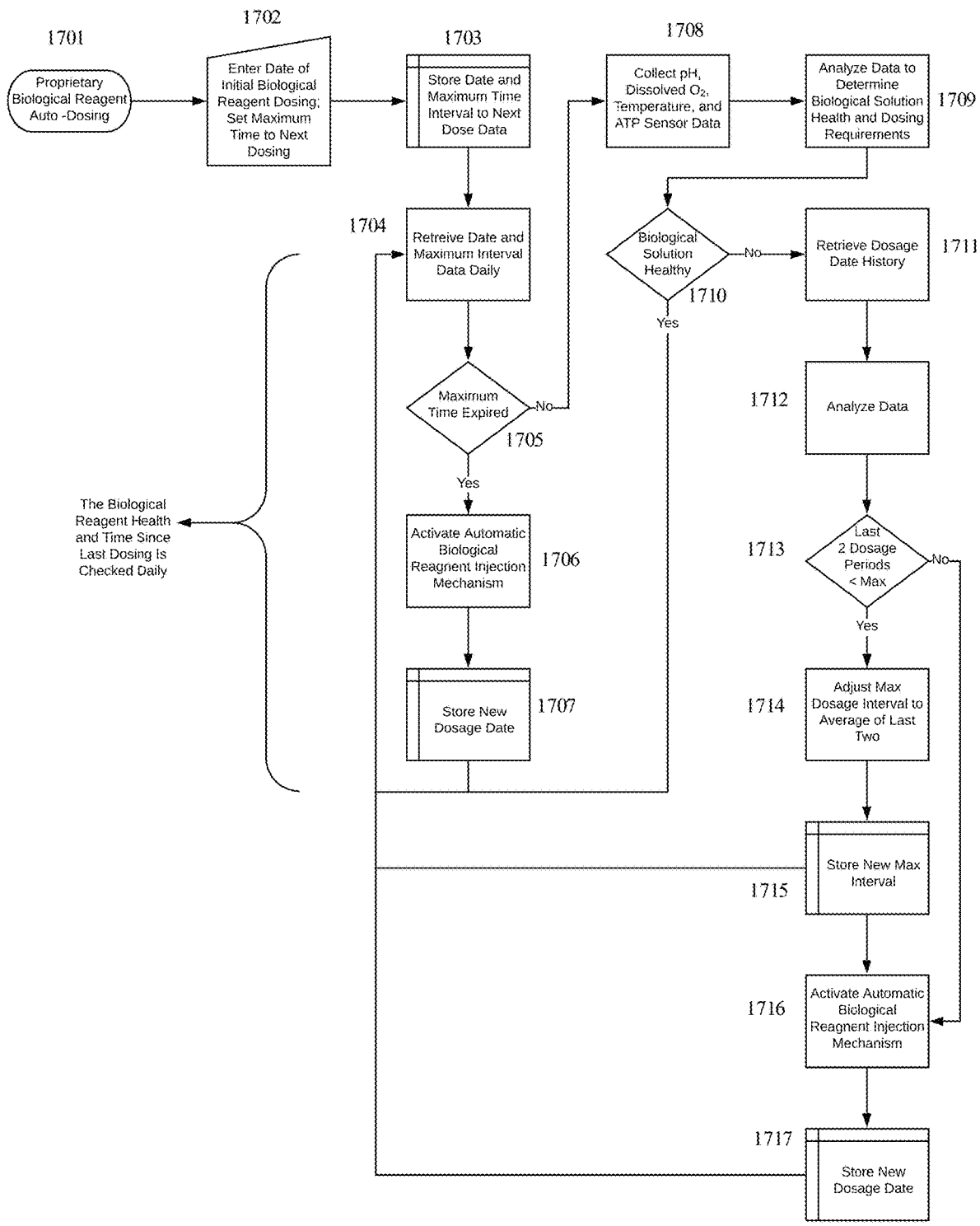

FIG. 17 is a flow chart for biological reagent dosing. For example, in this process the system starts in step 1701 wherein proprietary biological reagent is auto dosed into an existing volume of water or water and reagent solution stored in a container such as container 40. Next, in step 1702 the user can enter in the date and time of the biological reagent dosing, and then set the maximum time to the next dosing. As described above the data entry can be through either the display screen 216 or through the Next, in step 1703 the system can store the date and maximum time interval to the next dose in the memory such as in memory 204. Next, in step 1704 the system such as processor 202 can retrieve the date and maximum interval data daily. In step 1705 the system determines whether the maximum time has expired. If the maximum time has expired, the system proceeds to step 1706 wherein it activates automatic biological reagent injection in step 1706. Next, in step 1707 the system can store the new dosage date in memory 204.

Alternatively, if the maximum time has not expired, then in step 1708 the system can collect the following information about the biological reagent solution: pH, dissolved $O_2$, as well as Temperature and ATP sensor data. Next, in step 1709 the system proceeds to analyze the date to determine the biological solution health and dosing requirements. Next, in step 1710 the system determines whether the biological solution is healthy. If for example the biological solution is determined to be healthy, then the process proceeds back to step 1704 to retrieve the date and maximum interval data daily or on a more frequent basis. Alternatively, if the system determines that the biological solution is not healthy in step 1711 the system can retrieve the dosage date and history. Next, in step 1712 the system can analyze the data. Next, in step 1713 the system can determine the last two dosage periods to determine whether these last two dosage periods are below the maximum periods. Next, in step 1714, the system can adjust the maximum dosage interval to the average of the last two dosage periods. Next, in step 1715 the system can store the new max interval such as in memory 204. Next, in step 1716, the system proceeds to activate the automatic biological reagent injection mechanism. This step 1716 can also be triggered automatically if the last two dosage periods were greater than the standard max dosage period and the time period has exceeded the pre-set max dosage period. Next, in step 1717 the system can store the new dosage date, and then start over again.

Figure 18:
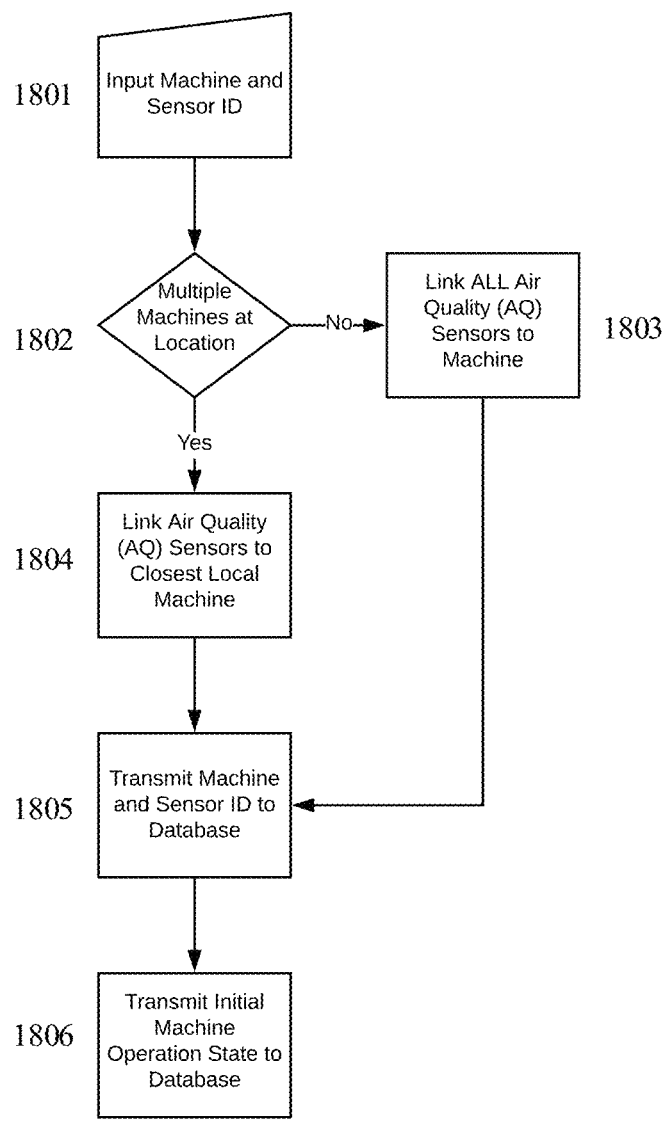

FIG. 18 shows the data driven air purification machine control process wherein this process starts in step 1801 wherein the user inputs machine and sensor identification. Next, in step 1802 the network tracks multiple machines in different locations such as shown in FIG. 15B which shows controller 200, controller 220, and controller 224. Each of these controllers represent an associated machine or device that is being tracked by server 218. Server 218 is in continuous communication with the different controllers and is configured to be updated on a continuous basis. Next, in step 1803, if there are not multiple machines at one location, the system can link all air quality sensors to a particular machine in step 1803. Next, in step 1804 the system can link air quality AQ sensors to the closes local machine. Next in step 1805 the system is configured to transmit machine and sensor ID to the Database. The transmission of this machine and sensor ID information to the server/database allows for the server 218 to collect data from all of the different controllers/devices which are located in different locations. Next, in step 1806 the system can transmit the initial machine operation state to the database. The storage of this information can then be used for future guidelines on running the machines.

Figure 19:
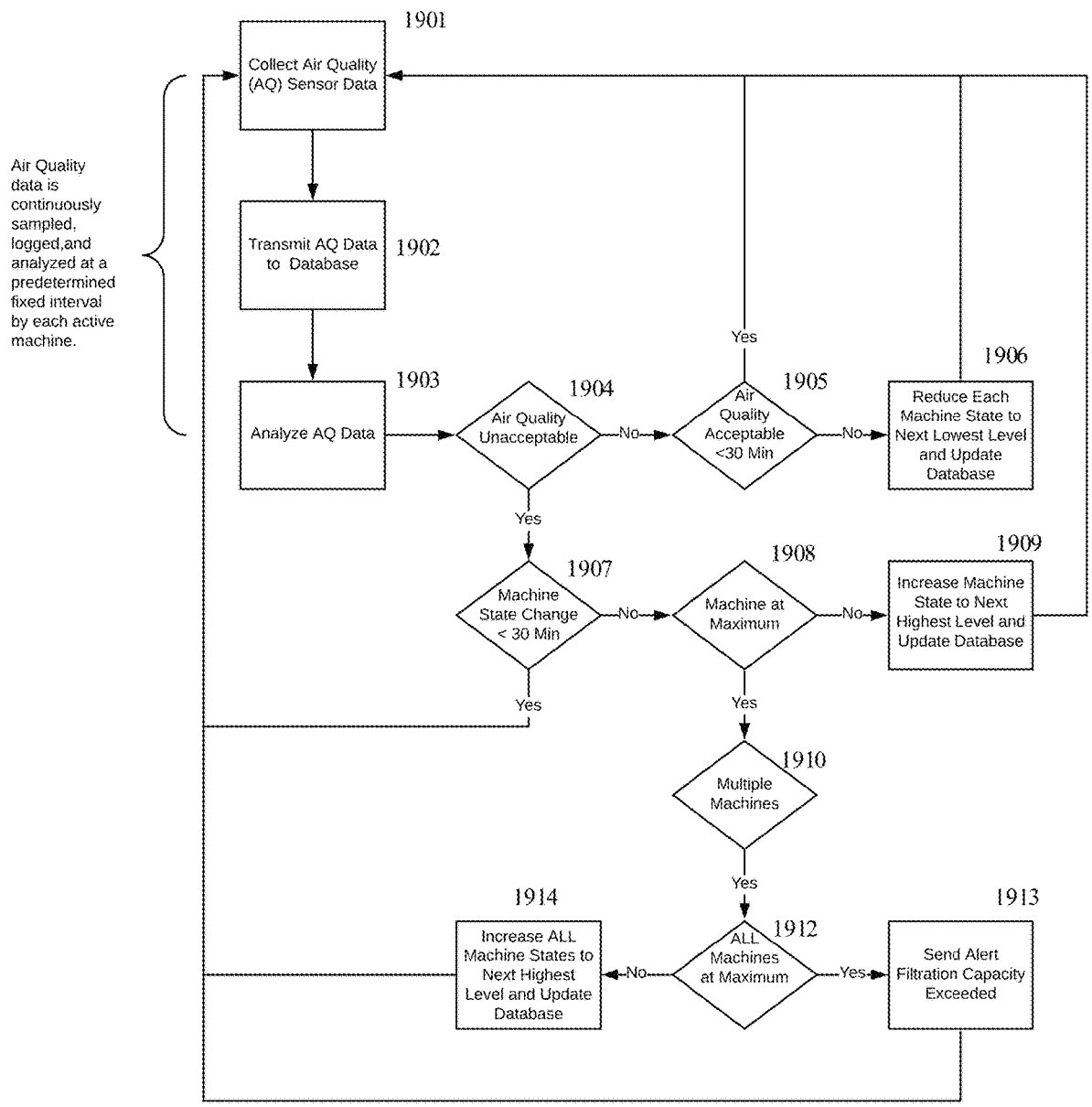

FIG. 19 is a process for monitoring air quality. The process starts in step 1901 wherein the system collects air quality sensor data (AQ). Next in step 1902 the system transmits air quality data (AQ) data to the database stored in server 218. Next, in step 1903 the system can analyze AQ data and then in step 1904 determine if the air quality is acceptable. For all of the embodiments disclosed herein the determination of whether the ambient air quality is acceptable occurs by determining whether the presence of at least one of volatile organic compounds, particulate matter, pollen or other organics or other impurities in the air such as smoke are present in a volume or amount that is above a predetermined value. These predetermined values can be stored in a database in a server such as server 218 and then stored in a memory such as memory 204 (See FIG. 15A).

If the air quality is not acceptable then the system proceeds to step 1905 wherein the system determines if the air quality is acceptable within less than 30 minutes. Next, in step 1906 the system can reduce each machine state to the next lowest level and then update the database.

Alternatively, if the air quality is determined to be unacceptable then the system will change its state in less than 30 minutes. If the machine cannot change its state, then the system determines if the machine is at a maximum in step 1908. If the machine is not at its maximum state, then in step 1909 the machine can increase its state, such as increase the RPM of the fan such as fan 150 to process more air and to remove more particulates. After step 1909 the process can proceed back to step 1901 to collect air quality sensor data as well.

Alternatively, the system can proceed to step 1910 wherein it determines whether there are multiple machines present. If all of the machines are determined present, wherein all of the machines in a region are determined to be present. If the system determines in step 1912 that all of the machines are not at a maximum, then the process proceeds to step 1914 which proceeds to increase all machine states to the next highest level, and then the system or database is updated. The process then proceeds back to step 1901 to collect air quality and sensor data. If the system determines in step 1912 that all of the machines are at a maximum, then the process proceeds to step 1913 which proceeds to send an alert that filtration capacity has been exceeded.

Ultimately, this system and process includes a network of air purification devices which are configured to collect and analyze data and to record this data and then control multiple different air purification devices across an integrated network based upon the data that is taken into the system.

Ultimately microprocessor 202 is configured to control the sensors 209, 211, 213 and 215 and to read information from these two sensors. In addition, microprocessor 202 is configured to control pump 210, fan 206 and valves 212 and 214. Furthermore microprocessor 202 is configured to read information from memory 204 and to send information to memory 204 as well as communicate with transceiver 208. Microprocessor is also configured to communicate with GPS transceiver 219 which then passes on the GPS coordinates of the controller 200. GPS transceiver 219 is an optional component. Alternatively, controller 200 can receive coordinate information from a portable electronic device 223 during setup, or through a manual setup designating the location of the device. For example, because microprocessor 202 can receive information from any one of sensors 209, 211, 213 and 215 it can then selectively run fan 206 at a higher state or higher rpm to draw more air through the system based upon a predetermined set of values stored in memory 204. Alternatively, or in addition, microprocessor can run pump 210 faster as well to move more fluid in the form of water and bioreactive solution through the system. Furthermore, based upon a predetermine time or other predetermined settings microprocessor can selectively open any one of valves 212 and/or 214 to allow water to flow into the container from a common water feed. Furthermore, microprocessor 202 can selectively operate bioreactive dosing agent 217 to add more bioreactive component to the bioreactive solution of bioreactive component and water. Microprocessor 202 can selectively operate bioreactive dosing agent 217 which can be in the form of a feed such as a screw feed or a valve, based upon a predetermined set of values which are stored in memory 204 and then separately conveyed to microprocessor 202. These predetermined set of values are based upon time and/or use such as a factor of time and the flow rate of pump 210 and/or the rpm of fan 206. Alternatively, microprocessor 202 can sound an alarm such as alarm 207 which is then used to indicate whether more water needs to be added, more bioreactive component, needs to be added or whether the device should be serviced.

Accordingly, while at least one embodiment of the present invention have been shown and described, it is to be understood that many changes and modifications may be made thereunto without departing from the spirit and scope of the invention as defined in the appended claims.

What is claimed is:

1. An air purifying machine comprising:
    a) at least one housing;
    b) a plurality of cores wherein each core is disposed in said at least one housing;
    c) at least one fan disposed in said at least one housing;
    d) at least one pump disposed in said at least one housing, said at least one pump configured to circulate a fluid inside of said at least one housing;

wherein said plurality of cores comprise at least two cores disposed inside of said at least one housing comprising a first core and a second core, wherein said second core is disposed inside of said first core and wherein said second core is not concentric with said first core.

2. The air purifying machine as in claim 1, wherein said second core is disposed adjacent to said first core in said at least one housing.

3. The air purifying machine as in claim 1, wherein said second core has a plurality of holes disposed in at least one side of the second core.

4. The air purifying machine as in claim 1, wherein said first core has a larger diameter than said second core.

5. The air purifying machine as in claim 1, further comprising at least one tray for receiving a fluid.

6. The air purifying machine as in claim 5, wherein said at least one tray comprises a top and a bottom section.

7. The air purifying machine as in claim 6, wherein said bottom section of said at least one tray has a plurality of holes in it.

8. The air purifying machine as in claim 1, further comprising at least one channel coupled to said at least one pump, wherein said channel extends up from a bottom section of said first and second core to said at least one tray.

9. The air purifying machine as in claim 8, wherein said at least one channel comprises a tube.

10. The air purifying machine as in claim 9, further comprising at least one valve coupled to the tube, wherein said at least one valve is configured to shut off fluid flow in said tube.

11. The air purifying machine as in claim 1, further comprising at least one microprocessor, wherein said at least one microprocessor is configured to control said at least one pump.

12. The air purifying machine as in claim 11, further comprising at least one water inlet and at least one valve, wherein said at least one microprocessor is configured to control said at least one valve.

13. The air purifying machine as in claim 12, wherein said at least one valve is a dual solenoid valve.

14. The air purifying machine as in claim 1, further comprising at least one sensor.

15. The air purification machine as in claim 1, wherein said at least one sensor comprises at least one of a volatile organic compound sensor, a particulate sensor and a humidity sensor.

* * * * *